United States Patent
Sogard et al.

(10) Patent No.: US 8,062,309 B2
(45) Date of Patent: Nov. 22, 2011

(54) DEFECT OCCLUSION APPARATUS, SYSTEM, AND METHOD

(75) Inventors: David J. Sogard, Brooklyn Park, MN (US); Leonard B. Richardson, Maple Grove, MN (US); Kent D. Harrison, Maple Grove, MN (US); Diane M. Sheahen, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1404 days.

(21) Appl. No.: 11/207,249

(22) Filed: Aug. 19, 2005

(65) Prior Publication Data

US 2007/0060858 A1    Mar. 15, 2007

(51) Int. Cl.
*A61B 17/00* (2006.01)
(52) U.S. Cl. ..................................................... 606/142
(58) Field of Classification Search .................. 606/139, 606/142, 143, 232; 600/101, 114
See application file for complete search history.

(56) References Cited

U.S. PATENT DOCUMENTS

| | | | |
|---|---|---|---|
| 5,370,675 A * | 12/1994 | Edwards et al. | ............... 607/101 |
| 5,749,889 A | 5/1998 | Bacich et al. | |
| 5,769,790 A | 6/1998 | Watkins et al. | |
| 5,919,200 A | 7/1999 | Stambaugh et al. | |
| 5,944,738 A | 8/1999 | Amplatz et al. | |
| 6,007,514 A | 12/1999 | Nita | |
| 6,024,718 A | 2/2000 | Chen et al. | |
| 6,352,503 B1 * | 3/2002 | Matsui et al. | ................. 600/104 |
| 6,378,501 B1 | 4/2002 | Hisato et al. | |
| 6,458,100 B2 | 10/2002 | Roue et al. | |
| 6,482,224 B1 | 11/2002 | Michler et al. | |
| 6,645,225 B1 | 11/2003 | Atkinson | |
| 6,650,923 B1 | 11/2003 | Lesh et al. | |
| 6,716,184 B2 | 4/2004 | Vaezy et al. | |
| 6,755,790 B2 | 6/2004 | Stewart et al. | |
| 6,776,784 B2 | 8/2004 | Ginn | |
| 7,566,300 B2 * | 7/2009 | Devierre et al. | ............... 600/104 |
| 7,621,925 B2 * | 11/2009 | Saadat et al. | ................... 606/139 |
| 7,678,133 B2 * | 3/2010 | Modesitt | ......................... 606/216 |
| 7,837,619 B2 * | 11/2010 | Sogard et al. | ................... 600/139 |
| 2002/0099390 A1 * | 7/2002 | Kaplan et al. | .................. 606/139 |
| 2002/0103459 A1 * | 8/2002 | Sparks et al. | ............. 604/164.13 |
| 2002/0107531 A1 | 8/2002 | Schreck et al. | |

(Continued)

FOREIGN PATENT DOCUMENTS

WO        9713463        4/1997

(Continued)

OTHER PUBLICATIONS

International Search Report, Nov. 22, 2006, 5 pgs.

(Continued)

*Primary Examiner* — Julian Woo
*Assistant Examiner* — Christopher L Templeton
(74) *Attorney, Agent, or Firm* — Brooks, Cameron & Huebsch, PLLC

(57) ABSTRACT

Methods, apparatus, and systems for occluding a multiplicity of parallel membranes, such as found in a patent foramen ovale (PFO). Methods, apparatus, and systems include the use of a positioning device that can be seated on the limbus of the septum secundum (SS). The positioning device includes a piercing member that can pierce the SS and septum primum (SP). The positioning device also includes a fastening member that can engage the SS and SP to fasten the tissues and occlude a PFO.

26 Claims, 19 Drawing Sheets

U.S. PATENT DOCUMENTS

| | | | |
|---|---|---|---|
| 2002/0173688 A1 | 11/2002 | Chen et al. | |
| 2002/0183787 A1 | 12/2002 | Wahr et al. | |
| 2003/0013971 A1 | 1/2003 | Makin et al. | |
| 2003/0045901 A1 | 3/2003 | Opolski | |
| 2003/0050665 A1 | 3/2003 | Ginn | |
| 2003/0144694 A1 | 7/2003 | Chanduszko et al. | |
| 2003/0181945 A1 | 9/2003 | Opolski et al. | |
| 2003/0191495 A1 | 10/2003 | Ryan et al. | |
| 2003/0208232 A1 | 11/2003 | Blaeser et al. | |
| 2003/0216759 A1* | 11/2003 | Burbank et al. | 606/157 |
| 2003/0225421 A1 | 12/2003 | Peavey et al. | |
| 2004/0073242 A1 | 4/2004 | Chanduszko | |
| 2004/0087968 A1 | 5/2004 | Core | |
| 2004/0092973 A1 | 5/2004 | Chanduszko | |
| 2004/0093017 A1 | 5/2004 | Chanduszko | |
| 2004/0098121 A1 | 5/2004 | Opolski | |
| 2004/0127855 A1 | 7/2004 | Core | |
| 2004/0127917 A1 | 7/2004 | Ginn | |
| 2004/0133236 A1 | 7/2004 | Chanduszko | |
| 2004/0158264 A1* | 8/2004 | Adams et al. | 606/139 |
| 2004/0176788 A1 | 9/2004 | Opolski | |
| 2004/0176797 A1 | 9/2004 | Opolski | |
| 2004/0176799 A1 | 9/2004 | Chanduszko et al. | |
| 2004/0193147 A1 | 9/2004 | Malecki et al. | |
| 2004/0230185 A1 | 11/2004 | Malecki et al. | |
| 2004/0243122 A1 | 12/2004 | Auth et al. | |
| 2004/0267191 A1 | 12/2004 | Gifford, III et al. | |
| 2004/0267306 A1 | 12/2004 | Blaeser et al. | |
| 2005/0021016 A1 | 1/2005 | Malecki et al. | |
| 2005/0034735 A1 | 2/2005 | Deem et al. | |
| 2005/0043759 A1 | 2/2005 | Chanduszko | |
| 2005/0059983 A1 | 3/2005 | Opolski et al. | |
| 2005/0059984 A1 | 3/2005 | Chanduszko et al. | |
| 2005/0070923 A1 | 3/2005 | McIntosh | |
| 2005/0070952 A1 | 3/2005 | Devellian | |
| 2005/0080406 A1 | 4/2005 | Malecki et al. | |
| 2005/0080430 A1 | 4/2005 | Wright, Jr. et al. | |
| 2005/0085843 A1 | 4/2005 | Opolski et al. | |
| 2005/0101984 A1 | 5/2005 | Chanduszko et al. | |
| 2005/0119524 A1* | 6/2005 | Sekine et al. | 600/114 |
| 2005/0131401 A1 | 6/2005 | Malecki et al. | |
| 2005/0131460 A1 | 6/2005 | Gifford, III et al. | |
| 2005/0228283 A1 | 10/2005 | Gifford et al. | |
| 2005/0251210 A1 | 11/2005 | Westra et al. | |
| 2005/0267495 A1* | 12/2005 | Ginn et al. | 606/151 |
| 2007/0043318 A1 | 2/2007 | Sogard et al. | |
| 2007/0043337 A1 | 2/2007 | McAuley | |

FOREIGN PATENT DOCUMENTS

| | | |
|---|---|---|
| WO | WO 02/17809 A1 | 3/2002 |
| WO | WO 2005/027753 A1 | 3/2005 |
| WO | WO 2005/039419 A1 | 5/2005 |

OTHER PUBLICATIONS

International Search Report, Dec. 1, 2006, 8 pgs.

* cited by examiner

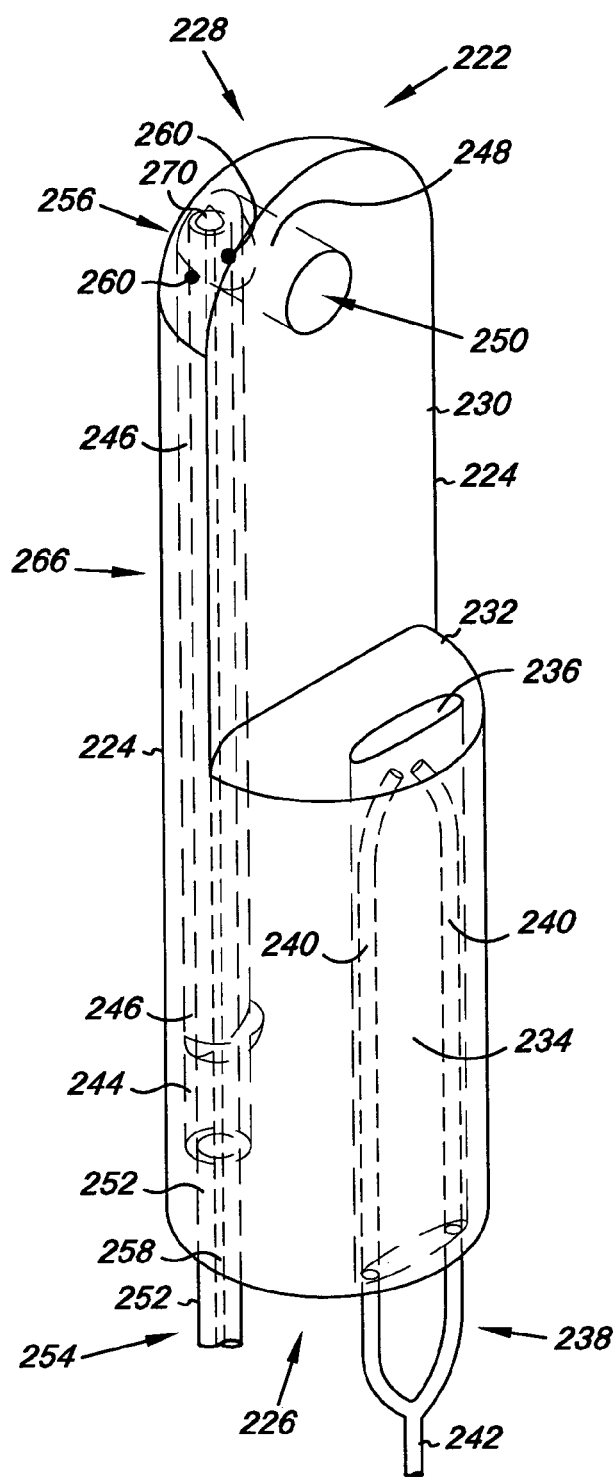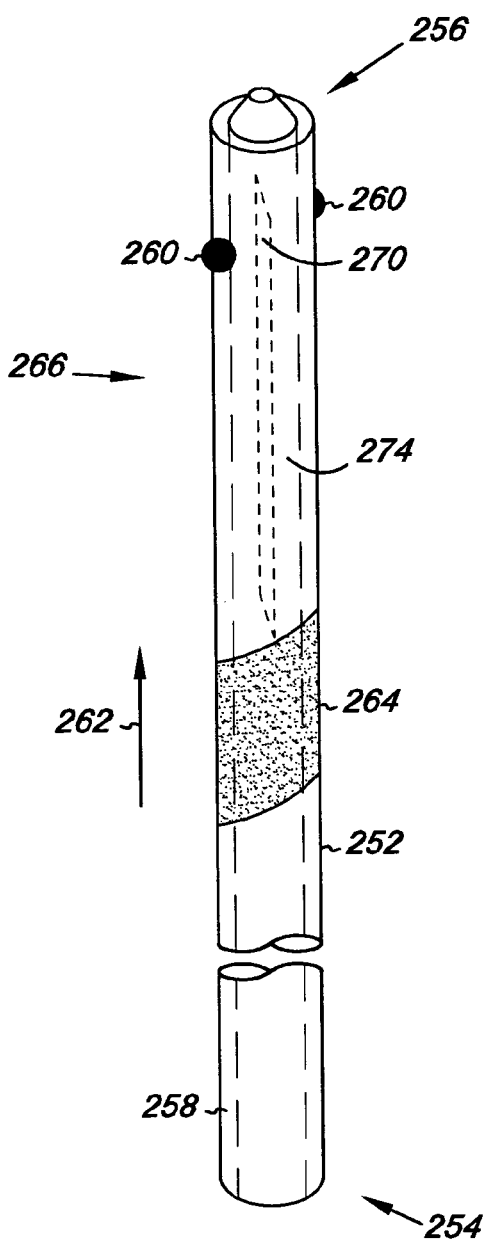
Fig. 2A
Fig. 2B

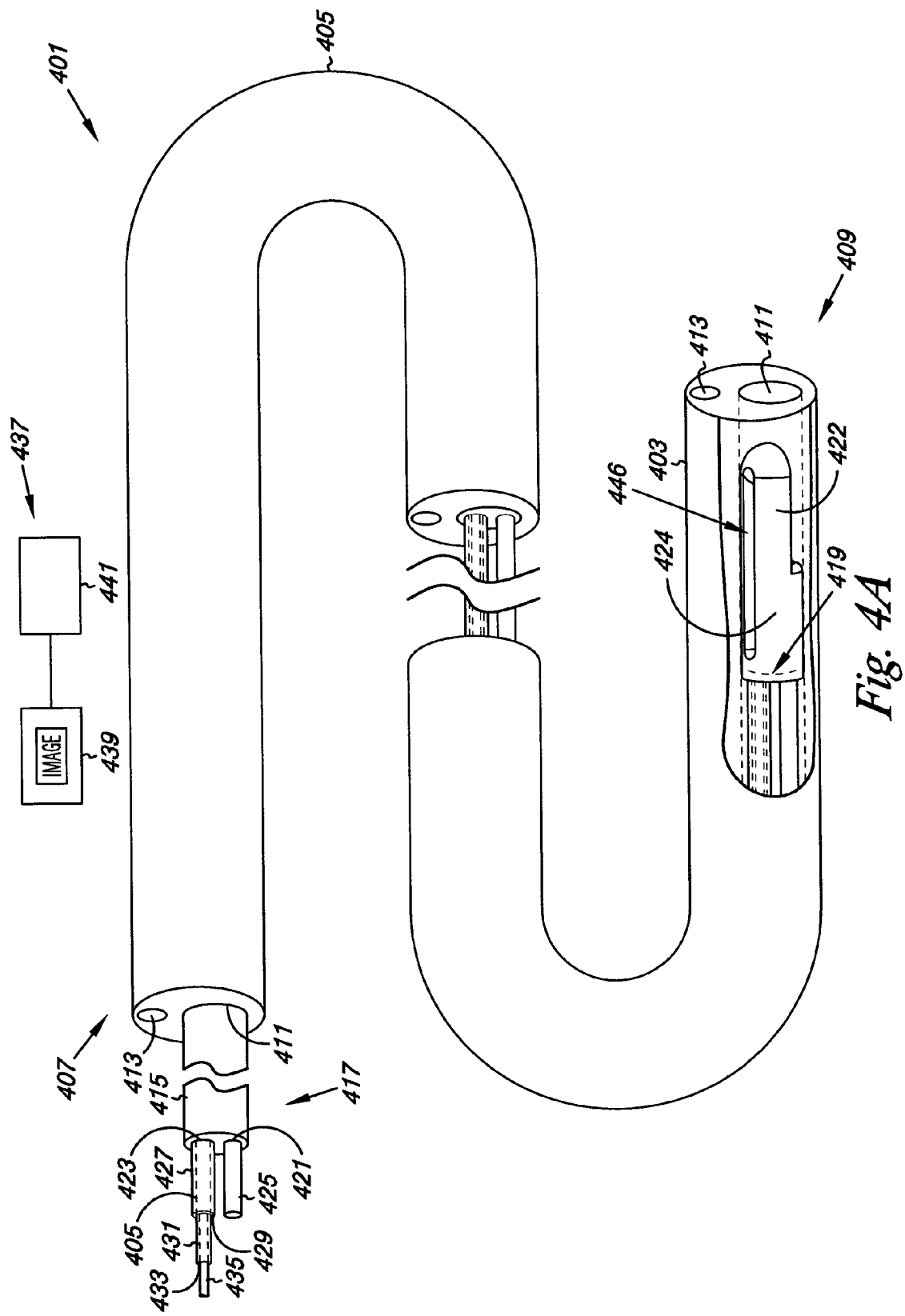

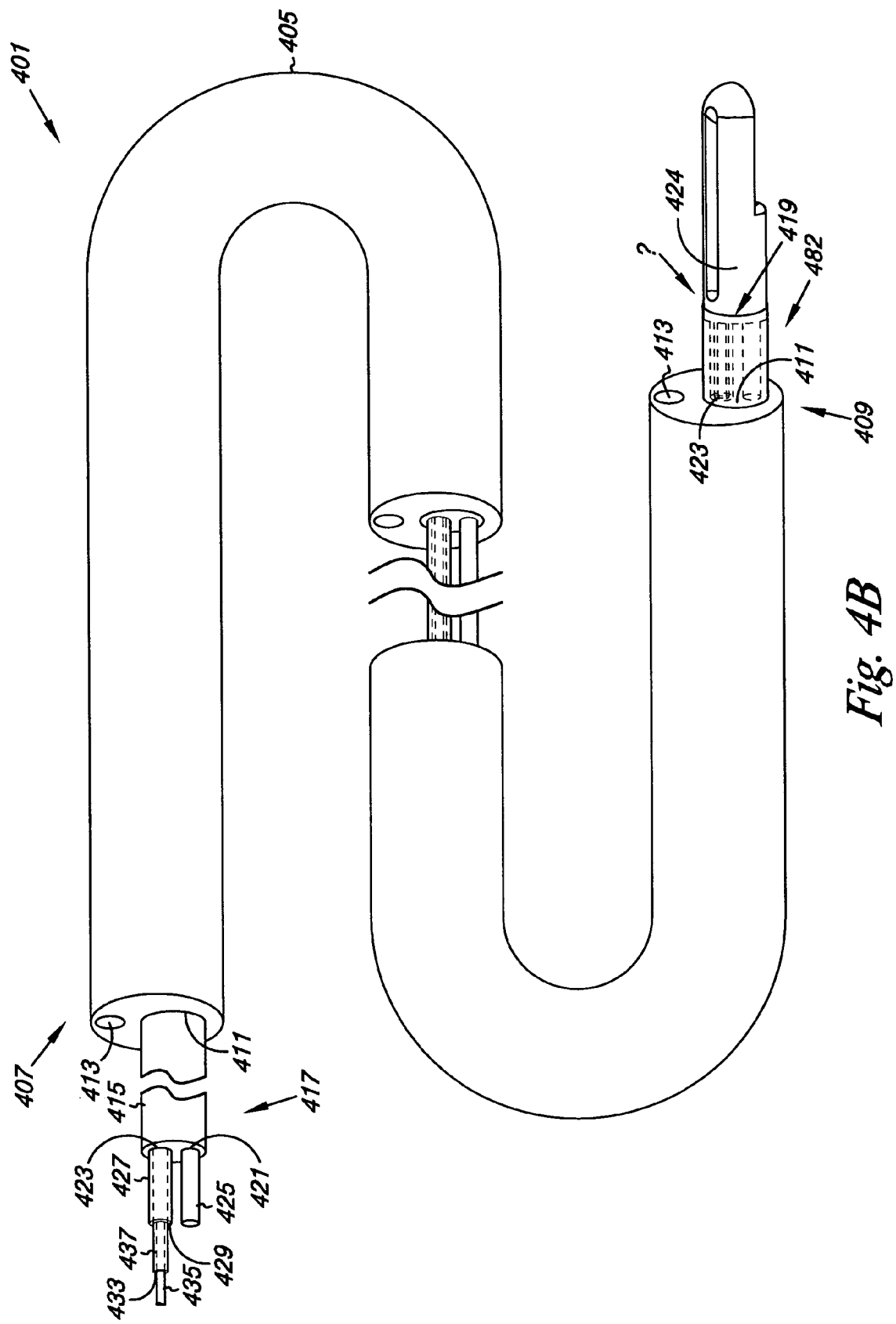

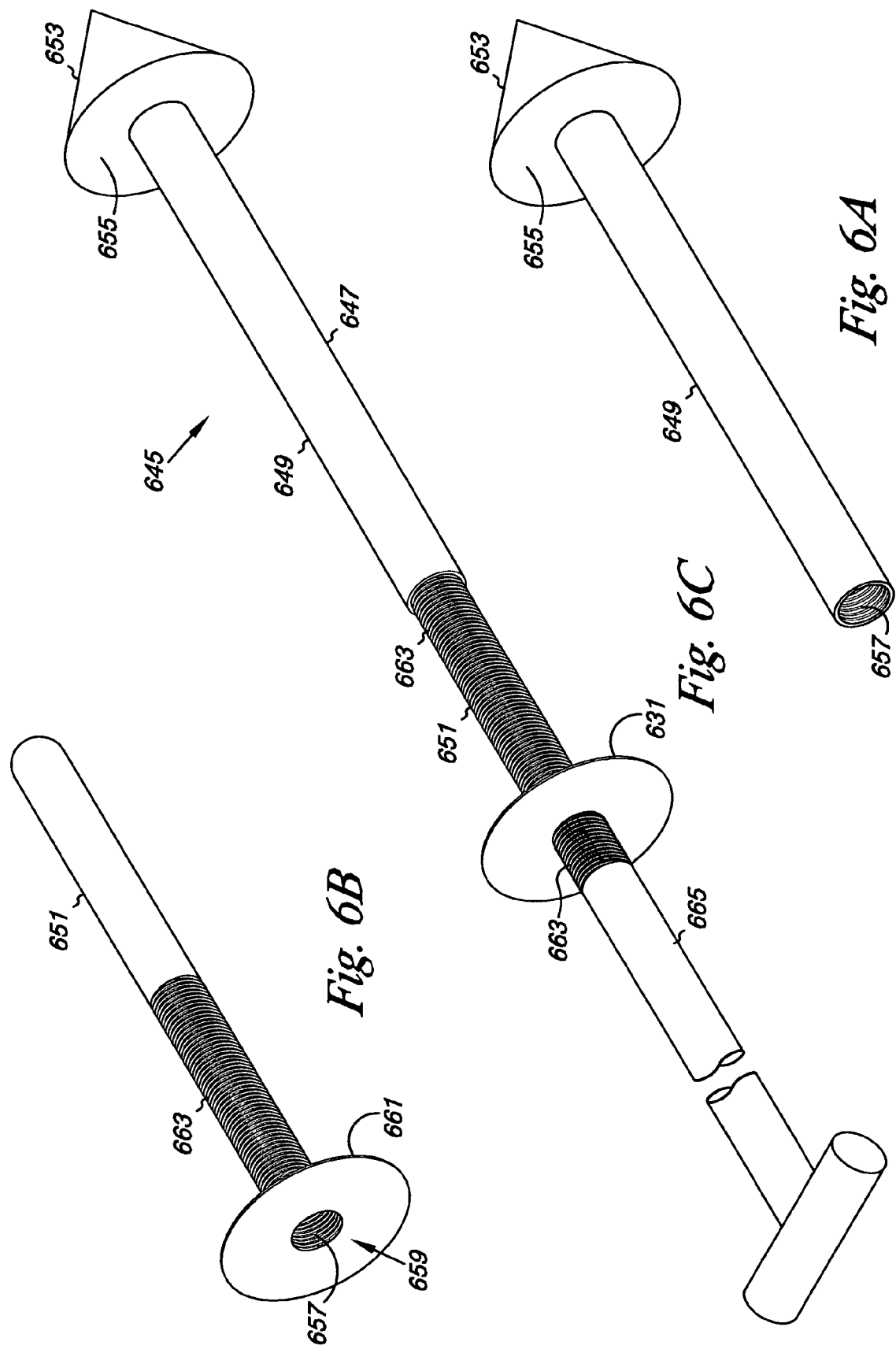

DEFECT OCCLUSION APPARATUS, SYSTEM, AND METHOD

FIELD OF THE INVENTION

The present invention relates generally to apparatus, systems, and methods for use in a heart, more particularly to apparatus, systems, and methods to seal a multiplicity of parallel membranes, such as found in a patent foramen ovale.

BACKGROUND

The human heart is divided into four chambers. These include the right atrium, the right ventricle, the left atrium, and the left ventricle. The right atrium and right ventricle are divided from the left atrium and left ventricle by a muscular wall called the septum. The atrial septum is the wall separating the atria, and the ventricular septum is the wall separating the ventricles.

Early in fetal development the two atria (i.e., left and right atriums) are a single chamber. A wall or membranous structure develops from the superior aspect of the atrial chamber and extends superiorly toward the base of the atrial chamber. This membrane is the septum primum (SP). As the SP seals to the base of the chamber, it is dissolved away at the superior attachment, creating a passageway for blood to travel from the right atria to the left atria (bypassing the developing lungs). At about the same time, a second membrane develops from the superior aspect of the right atrium and extends inferiorly. This membrane is the septum secundum (SS). It fuses with the SP along the walls of the atria, but does not extend to the base of the atria. The inferior portion of the SS is named the limbus. The two membranes form a passage defined by thin tissue (SP) and thick tissue (SS) that extends from the right atria to the left atria. This passage is named the foramen ovale. The portion of the SP that comprises the left side of the foramen ovale is named the fossa ovalis. The limbus of the SS is distinct from the fossa ovalis of the SP in that it is thicker and more muscular.

Upon birth blood must be diverted into the lungs of the newborn. One event that enables this is an increase in pressure within the left atrium relative to the right atrium. This pressure reversal effectively closes the foramen ovale and eliminates the shunting of blood from right to left. In most people, the SP and SS membranes that form the passage of the shunt fuse and the passage is eliminated. However, in a minority of people, these membranes do not fuse effectively and the shunt remains sealed by pressure, but the passage remains viable, or patent. This condition is named patent foramen ovale (PFO). In unusual circumstances the pressure in the right atrium can exceed that in the left atrium, allowing passage of blood through the PFO. This would typically be inconsequential, except when the venous (right atrial) blood contains thrombotic debris that is normally eliminated by thrombolytic mechanisms in the lungs. In this case, a clot can travel to the left atria and become an embolic risk to the patient's health through myocardial infarction or stroke.

BRIEF DESCRIPTION OF THE DRAWINGS

FIG. 2A illustrates a positioning device according to one embodiment of the present invention.

FIG. 2B illustrates an elongate structure of the positioning device in a first position according to one embodiment of the present invention.

FIGS. 4A-4C illustrate various embodiments of a system according to the teachings of the present invention.

FIGS. 6A-6C illustrate another embodiment of the piercing member according to one embodiment of the invention.

DETAILED DESCRIPTION

Figure 1:
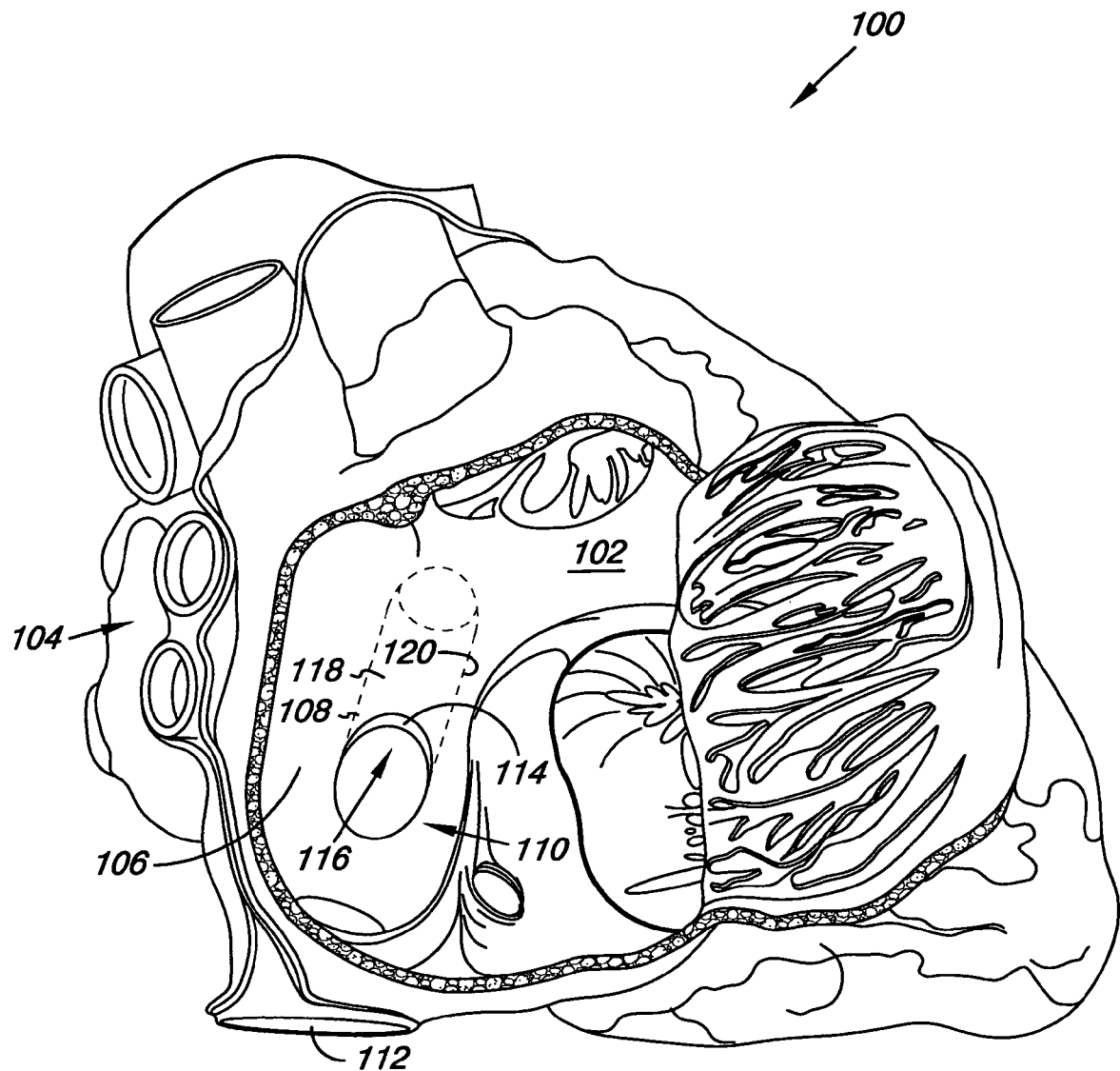
FIG. 1 illustrates an embodiment of a right lateral view of the heart.

Embodiments of the present invention are directed to methods, apparatus, and systems for occluding (i.e., sealing) a patent foramen ovale (PFO). As will be discussed in more detail herein, a positioning device on a delivery catheter can be seated on the septum secundum (SS) of the atrial septum, e.g., seated on the limbus of the SS. Seating the positioning device on the SS helps to locate the positioning device at a position on the atrial septum where two membranes, the SS and the septum primum (SP), lie parallel to one another. This position makes possible the use of the various embodiments described herein to seal a PFO, (e.g., seal the passage defined by the SS and SP). For example, in various embodiments, the SS and the SP can be pierced with a piercing member that extends from an elongate structure of the positioning device. As will be discussed herein, once the SS and SP have been pierced, the patent foramen ovale can be occluded with a fastening member releasably positioned within a lumen of the piercing member.

In some embodiments, the positioning device can include extension members that can be used to tighten thin tissue of the SP and/or thick tissue of the SS within the passage of a PFO prior to piercing those tissues. Thus, in various embodiments, by manipulating components of the positioning device (e.g., extension members and/or elongate structure, piercing member and fastening member) thick and/or thin tissue can be tightened, and pierced, and the PFO occluded.

In various embodiments, the positioning device can include an extension member that extend into the passage of a PFO while the elongate body of the positioning device remains in the right atrium. The extension members assure that the elongate body of the positioning device is correctly oriented with respect to the passage of the PFO. This positioning mechanism assures correct alignment for a piercing member contained within the elongate structure of the positioning device. These and other embodiments of the present invention are discussed herein.

The Figures herein follow a numbering convention in which the first digit or digits correspond to the drawing Figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of the positioning device according to the present invention.

In FIG. 1, a right lateral view of the heart 100 is shown with an opened right atrium 102. The heart 100 is divided into four chambers, which are referred to herein as the right atrium 102, a right ventricle, a left atrium 104 and a left ventricle. Heart 100 also includes a septal wall 106 that divides the four chambers of the heart. The portion of the septal wall 106 dividing the left and right atriums 102 and 104 is called the interatrial septum 108. The portion of the septal wall 106 dividing the left and right ventricle is called the ventricular septum.

As shown in FIG. 1, the fossa ovalis 110 is situated at the lower part of the atrial septum 108, above and to the left of the orifice of the inferior vena cava 112. The limbus 114 of the septum secundum 118 is the pronounced anterosuperior margin of the fossa ovalis 110 within the right side (i.e., the right atrium 102) of the interatrial septum 108. It represents the inferior margin of the SS during fetal life.

The passage 116 can be defined by surfaces of the SS (thick tissue) and surfaces of the SP (thin tissue) and extends between the right and left atriums 102 and 104. As used herein, the passage 116 is defined by surfaces of the SS and SP and can be used interchangeably with a PFO. The thick tissue 118 forms the right margin of the passage 116 and comprises the superior portion of the interatrial septum 108. Thus, the thick tissue 118 is located adjacent the limbus 114 and extends upward and rightward away from the limbus 114. The thin tissue 120 forms the left margin of the passage 116 and comprises the inferior portion of the interatrial septum 108 (i.e., below the thick tissue 118) and extends upward and rightward substantially parallel to the thick tissue 118 and toward the left atrium 104.

Figure 2C:
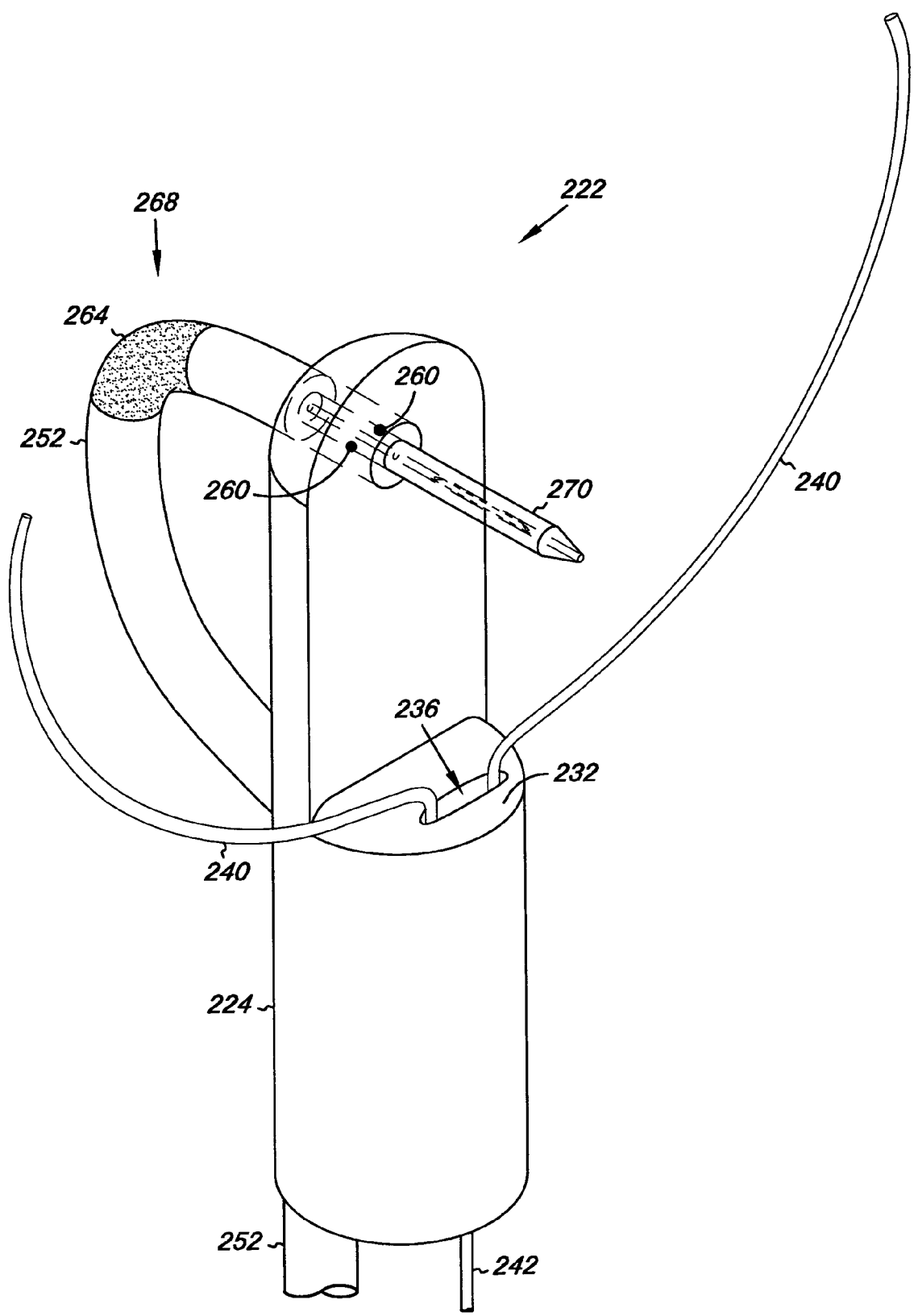
FIG. 2C illustrates the positioning device according to an additional embodiment of the present invention.

FIGS. 2A-2E illustrate various embodiments of the positioning device 222 that can be used to occlude a PFO according to the teachings of the present invention. As shown in FIG. 2A, positioning device 222 includes an elongate body 224 having a proximal end 226 and a distal end 228. The elongate body 224 includes a wall 230 that extends from the distal end 228 toward the proximal end 226. In the embodiment shown in FIG. 2A, the wall 230 includes a planar surface. However, in various embodiments, the wall 230 can include other types of surfaces. For example, in some embodiments, the wall 230 can include non-planar surfaces such as a convex surface or a concave surface.

The wall 230 extends toward the proximal end 226 to a ledge 232 that extends away from the wall 230. In one embodiment, the ledge 232 extends perpendicularly away from the wall 230 for a predetermined distance. The ledge 232 includes a planar surface whose outer edge defines a semi-circular shape. As will be discussed herein, the ledge 232 of the positioning device 222 allows the positioning device 222 to be seated on the limbus of the SS of a patient's heart.

Since the size and shape of the limbus can vary from patient to patient, the positioning device 222, including the wall 230 and the ledge 232 can include various shapes and sizes that can be based on the anatomical structures of a patient's heart including the limbus of the SS. For example, in some embodiments, the ledge 232 can have a surface defining various geometric shapes and sizes, including, but not limited to, convex shapes, concave shapes, recessed shapes, and irregular shapes, among others. In addition, in some embodiments, the ledge 232 can extend at various angles other than perpendicular from the wall 230 of the elongate body 224.

In various embodiments, the elongate body 224 of the positioning device 222 can be constructed from a number of materials. Examples of materials include, but are not limited to, metal, metal alloys, polymeric materials, natural and synthetic materials, etc.

The positioning device 222 includes a number of lumens that extend various lengths within the positioning device 222. In one embodiment, a first lumen 234 extends toward the ledge 232. As shown in FIG. 2A, the first lumen 234 extends toward ledge 232 and communicates with a ledge opening 236 defined by the surface of the ledge 232. In one embodiment, the first lumen 234 and the ledge opening 236 can accommodate the movement of a component positioned within the first lumen 234, as will be discussed herein.

As shown in FIG. 2A, the first lumen 234 includes surfaces defining an ovular cross-sectional shape. In various embodiments however, the first lumen 234 can include other cross-sectional shapes including, but not limited to, circular and polygonal cross-sectional shapes. In various embodiments, the cross-sectional shape of the first lumen 234 can be formed to accommodate a particular design of a component therein.

For example, in one embodiment, the component can be an extension member 238. As shown in FIG. 2A, the extension member 238 is extendably positioned within the first lumen 234 toward the ledge 232 of the elongate body 224. As used herein, an extendably positioned extension member 238 is an extension member having at least one arm 240 that can be moved within the first lumen 234 and through the ledge opening 236 such that the arm 240 extends away from the ledge 232 of the elongate body 224. In various embodiments, the arm 240 can extend away from the ledge 232 in various directions and in various planes, as will be discussed herein with respect to FIG. 3A.

In various embodiments, the extension member 238 can include one or more arms 240 and one or more bases 242. For example, in some embodiments, the extension member 238 can include two arms and two bases. And, in other embodiments, the extension member can include a single arm and a single base, as will be discussed herein with respect to FIGS. 3A-3F.

In the embodiments illustrated in FIGS. 2A and 2C, the extension member 238 includes two arms 240 that diverge from a base 242. The two arms 240 extend away from the ledge 232 both longitudinally and radially when moved through the ledge opening 236, as shown in FIG. 2C.

In various embodiments of the present disclosure, various components (e.g., extension member 238, a piercing member 270 and/or a fastening member 272, as will be discussed below with respect to FIGS. 2E-2I) of the positioning device 222 can be formed to include super elastic, linear elastic, and/or shape memory properties that allow the components to form varying shapes under varying conditions (e.g., strain, temperature, etc.). Specific examples of materials that can exhibit these properties can include various metals, metal alloys and polymers.

In various embodiments, the components can formed of the same material or a combination of materials and can include various layers. For example, in various embodiments, the extension member and/or fastening member can include a first layer formed a metal alloy core such as NiTi (Nitinol) to exhibit super elastic properties and a second layer formed over the core such as stainless steel or copper that can exhibit linear elastic properties. In some embodiments, the components can include a first layer formed of a linear elastic core, a second layer formed of a superelastic cover, and a third layer formed over the second layer formed of a shape memory polymer. These combinations of materials can provide the components with various properties and can be designed based upon the properties to be elucidated from a given component.

Shape memory and super elastic alloys can exhibit a particular shape at a cold temperature and another shape (e.g., a predefined shape) after being heated to a higher temperature. When being cooled to a lower temperature, the material retains its predefined shape but changes the structure to martensite, where the material can be easily deformed into different shapes at the lower temperature. Upon heating, the material changes back to austenite, where the deformation is recovered and the predefined shape is restored (one-way shape memory). Alloys can also have two-way shape memory that exhibit a reversible effect, with heat causing the change in shape which can be reversed by cooling. The phase that is stable at the lower temperature is called martensite and the phase stable at the higher temperature is called austenite.

A super elastic material such as a super elastic Nitinol typically displays a substantial loading plateau or super elastic plateau in its stress/strain curve. Such a material can be desirable in various embodiments because a super elastic alloy can provide structure that displays an enhanced ability of substantially recovering its shape without significant plastic deformation, relative to some other non-superelastic material upon the application and release of stress, for example, during insertion of an extension member or fastening member within various lumens of the positioning device and components of the positioning device.

A linear elastic alloy, for example a linear elastic nitinol, typically does not display a substantial loading plateau or super elastic plateau in its stress/strain curve. Instead, as recoverable strain increases, the stress continues to increase in a somewhat linear relationship until plastic deformation begins. Some linear elastic nickel-titanium alloys do not show any martensite/austenite phase changes that are detectable by differential scanning calorimetry (DSC) and dynamic mechanical thermal analysis (DMTA) over a large temperature range. Thus, the mechanical bending properties of such material are typically inert to the effect of temperature over a broad temperature range. As a result, the mechanical properties of the alloy at room temperature are substantially the same as the mechanical properties at body temperature. Thus, in various embodiments, the use of the linear elastic nickel-titanium alloy can provide for components of the positioning device that exhibit greater mechanical strength per unit strain than a comparable component made of superelastic nitinol.

Examples of suitable materials for the components of the positioning device include, but are not limited to, medical grade stainless steel (e.g., 316 L), titanium, tantalum, platinum alloys, niobium alloys, cobalt alloys, alginate, MP35N, aluminum alloys, chromium alloys, copper alloys, vanadium alloys, or combinations thereof. Other examples can include iron, super elastic Nitinol, non-super elastic Nitinol, or titanium. Examples of plastics can include shape memory plastics, polymers, and thermoplastic materials. Other materials can include bioabsorbable materials that are absorbed by the body over a period of time. Other materials are also contemplated.

In various embodiments, these materials can allow for forming and setting the predefined shape in the arms 240 that can resiliently flex to be compressed within the first lumen 234 in a collapsed configuration and then extend toward their predefined shape in an expanded configuration as the extension member 238 moves through the ledge opening 236 from the first lumen 234. For example, in one embodiment, the arms 240 have a predefined shape in their expanded state, as illustrated in FIG. 2C. When retracted within the first lumen 234, the arms 240 elastically bend so as to be held in compression in a collapsed configuration within the first lumen 234, as illustrated in FIG. 2A. As the arms 240 extend from the first lumen 234, the arms 240 return towards their predefined shape. As will be discussed herein, as the arms 240 return towards their predefined shape they can help to impart an expansion force upon the passage of a PFO in a manner that stretches the tissue of the passage in various directions.

In various embodiments, the extension member 238 can include various cross-sectional shapes. Examples of cross-sectional shapes of the extension member can include, but are not limited to, circular, ovular, and polygonal cross-sectional shapes, among others. In addition, in various embodiments, components that include varying layers of metals, metal alloys, and polymer materials can each include the same cross sectional shape or varying cross-sectional shapes.

The embodiments illustrated in FIGS. 3A-3F show examples of extension members 338 having a variety of predefined shapes in their relaxed state. The embodiments illustrated in FIGS. 3A-3F each include an extension member having one or more arms that extend away from the ledge 332, and one or more bases 342 that remain positioned within the positioning device. The embodiments illustrated in FIGS. 3A-3F are not meant to limit the extension members, but rather, to illustrate a few of the many types of extension members that are contemplated by this disclosure.

Figures 3A, 3B, 3C:
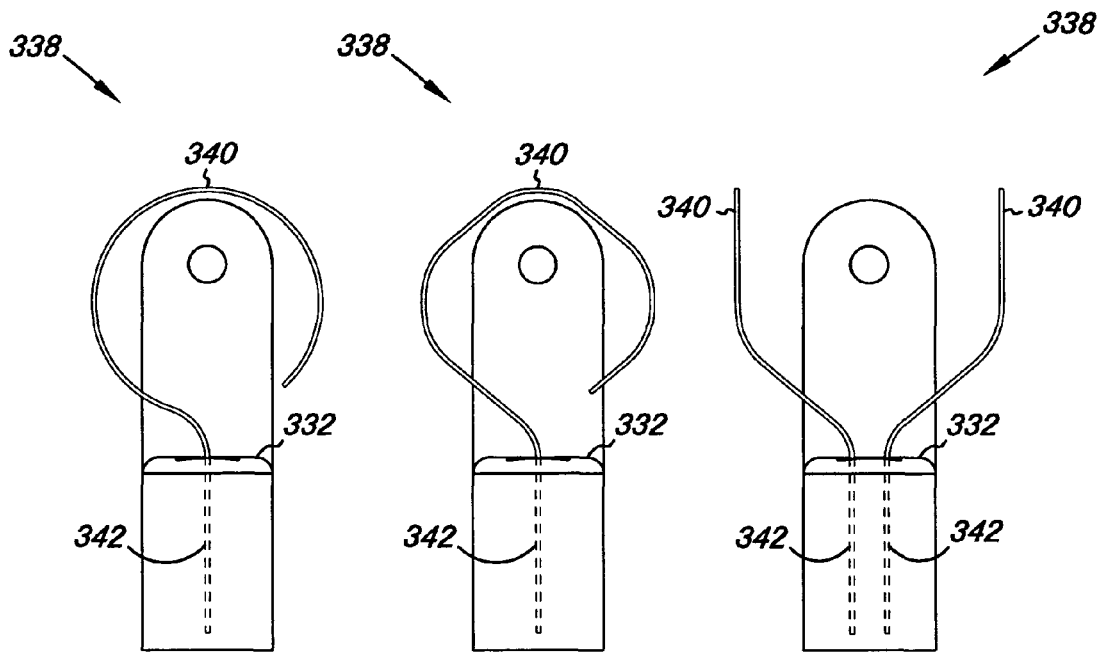
FIGS. 3A-3F illustrate various embodiments of an extension member of the positioning device according to the teachings of the present invention.

As shown in FIGS. 3A and 3B, the extension member 338 includes a single arm 340 and a single base 342. In some embodiments, the extension member 338 can include a number of arms and a number of bases. As shown in the embodiments illustrated in FIGS. 3C and 3D, the extension member 338 includes two arms 340 and two bases 342. In these embodiments, each arm 340 includes a base 342.

Figures 3D, 3E, 3F:
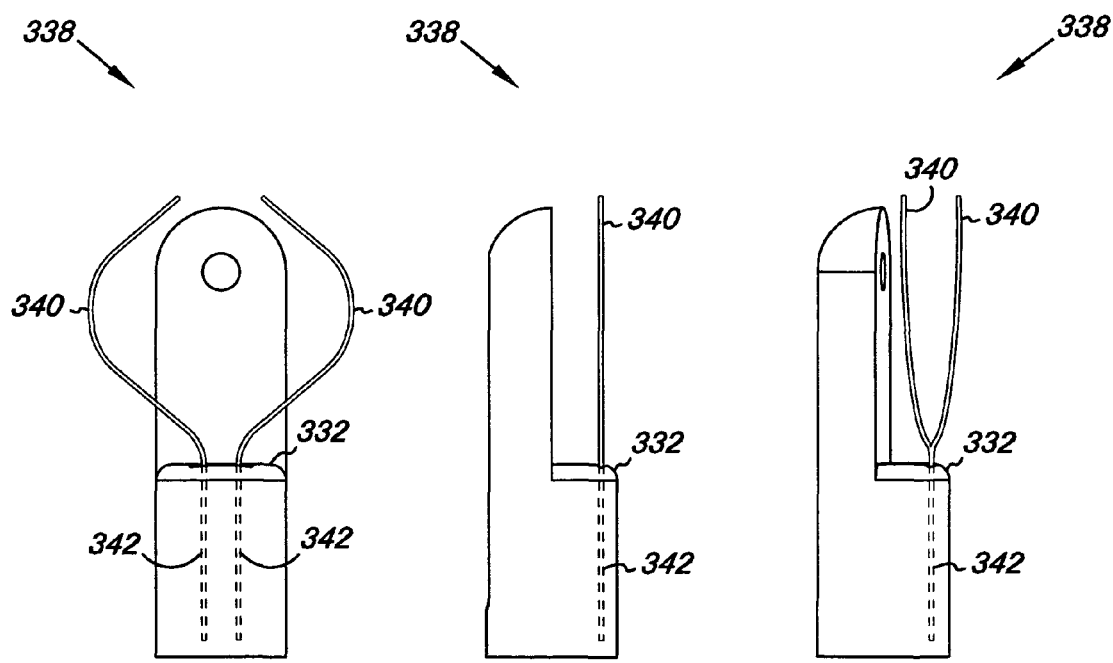

When the extension member 338 extends from the ledge 332, the arm or arms, depending upon the particular configuration of the extension member, can extend away in a single plane. For example, the embodiment illustrated in FIG. 3E includes a side view of an extension member 338 having two arms 340 and a single base 342. The extension member 338 illustrated in FIG. 3E is shown extending away from the ledge 332 of the elongate body 324 within the same plane. Since the arms 340 extend away from the ledge 332 within the same plane, and because a side view is illustrated in FIG. 3E, only one arm 340 can be seen in FIG. 3E.

In other embodiments, the extension member can extend away from the ledge in a number of different planes. For example, the embodiment illustrated in FIG. 3F illustrates a side view of an extension member 338 having two arms 340 and a single base 342. The extension member illustrated in FIG. 3F is shown extending away from the ledge 332 in two different planes. Since the arms 340 are shown as extending away from the ledge 332 in two different planes, and because a side view is illustrated in FIG. 3F, the two arms 340 of the extension member 338 can be seen in FIG. 3F.

Referring again to FIG. 2A, the positioning device 222 can include a second lumen 244. In various embodiments, the second lumen 244 can extend toward the distal end 228 of the elongate body 224. In the embodiment illustrated in FIG. 2A, the second lumen 244 extends toward the distal end 228 of the elongate body 224 to communicate with a channel 246. In this embodiment, the length of the second lumen 244 is short relative to the first lumen 234. In various embodiments however, the length of the second lumen 244 can be substantially longer as will be discussed herein.

The channel 246 is defined by the surface of the elongate body 224 and extends longitudinally between the second lumen 244 and a third lumen 248.

The third lumen 248 extends from a wall opening 250 defined by the surface of the wall 230. The third lumen 248 extends from the wall opening 250 and through the elongate body 224. In one embodiment, the third lumen 248 extends through the elongate body 224 to communicate with the channel 246, as discussed herein. In various embodiments, the third lumen 248 is perpendicular relative to the second lumen 244 and the channel 246. However, in some embodiments, the third lumen 248 can be angled other than perpendicularly relative to the second lumen 244 and the channel 246. And, in some embodiments, the third lumen can include curved surfaces that define a rotation point, as will be discussed more fully herein.

In the embodiments described herein, the second lumen 244, the channel 246, and the third lumen 248 can form a contiguous conduit in which components of the positioning device 222 can be positioned, extended, and/or retracted. For example, one such component can include an elongate structure 252, as illustrated in FIGS. 2A-2D. The elongate structure 252 includes a proximal end 254 and a distal end 256. The elongate structure 252 also includes a lumen 258 that extends longitudinally between the proximal end 254 and the distal end 256 of the elongate structure 252. In various embodiments, the elongate structure 252 can be extendably positioned within the second lumen 244 of the elongate body 224 toward the distal end 228 of the elongate body 224. In such embodiments, the elongate structure 252 passes through the second lumen 244, the channel 246, and to the third lumen 248, as shown in FIG. 2A.

In various embodiments, the elongate structure 252 can include a rotation point 260 along which the distal end 256 of the elongate structure 252 can rotate. As shown in FIGS. 2A-2D, the rotation point 260 includes two pivots coupled to an outer surface of the elongate structure 252. In turn, the pivots can be rotatably coupled to surfaces defining the channel 246 proximal the distal end 228 of the elongate body 224. In an alternative embodiment, the rotation point 258 can be defined by surfaces of the third lumen 248. In the alternative embodiment, the surfaces of the third lumen 248 can be formed to provide the rotation point 260 along which the distal end 256 of the elongate structure 252 can rotate, e.g., the surfaces of the third lumen 248 can be curved to define the rotation point such that the distal end of the elongate structure is guided by the curves as the elongate structure rotates, as will be discussed more fully herein. In such an embodiment, the elongate structure 252 would not require pivots.

The elongate structure 252 can include a flexible portion 264. The flexible portion 264 can be configured as a region of the elongate structure 252 that is more flexible as compared to other portions of the elongate structure 252. For example, in some embodiments, the flexible portion 264 of the elongate structure 252 can be formed of a flexible plastic and/or metal that can bend without obstructing the lumen 258 of the elongate structure 252. A portion of the elongate structure 252 extending from the flexible portion 264 toward the proximal end 254 of the elongate structure 252 can be formed of a semi-flexible plastic and/or metal that can bend, but not as easily as the flexible portion 264. And, a portion of the elongate structure 252 extending from the flexible portion 264 toward the distal end 256 of the elongate structure can be formed of a substantially rigid plastic and/or metal so as not to bend.

In the embodiments described herein, the rotation of the elongate structure 252 is accompanied by a predetermined bend of the elongate structure 252. That is, the rotation occurs along the rotation point 260 and the predetermined bend occurs along the flexible portion 264 of the elongate structure 252.

Figure 2D:
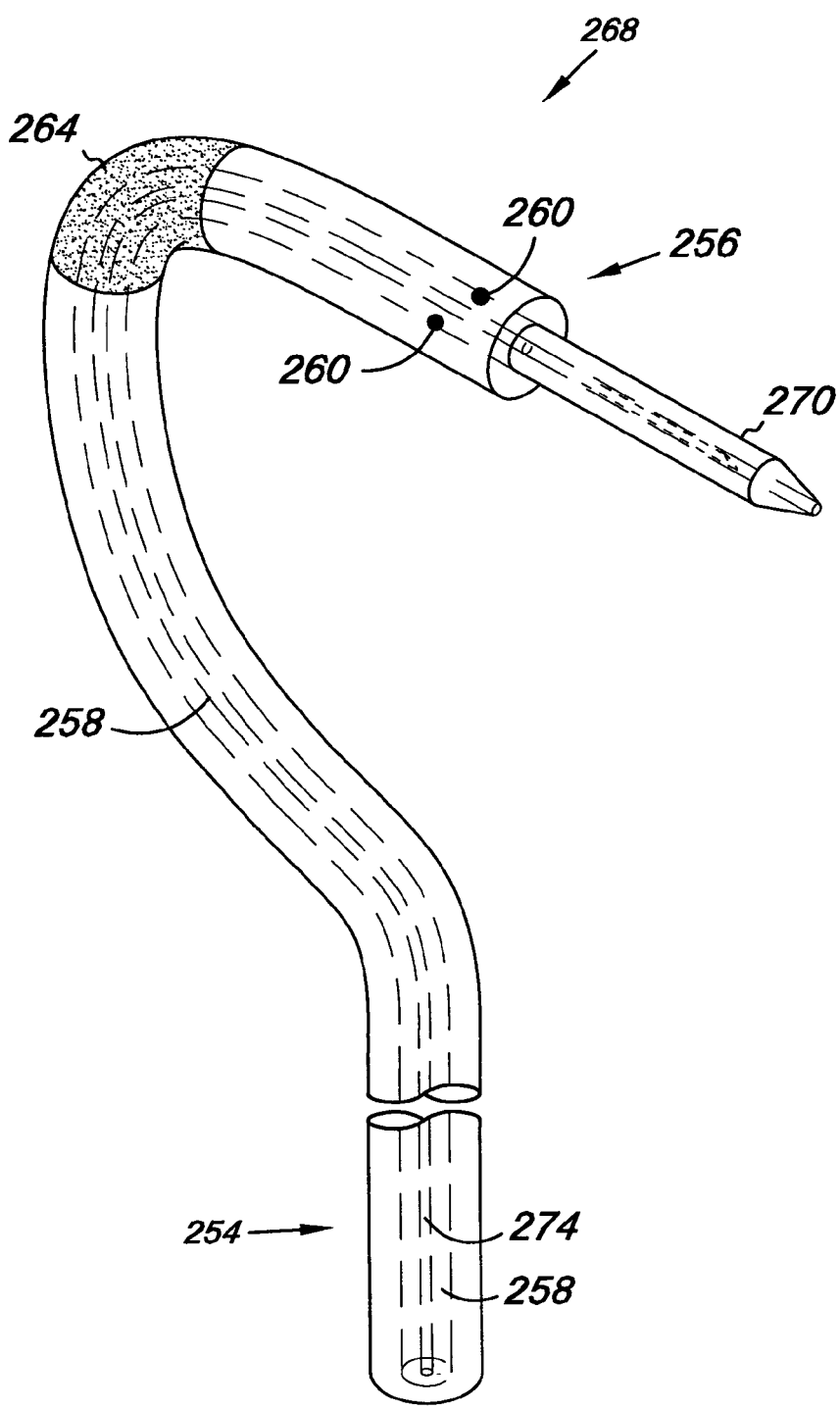
FIG. 2D illustrates the elongate structure of the positioning device in a second position according to one embodiment of the present invention.

The following description provides one example of the rotation and the bending of the elongate structure 252. In FIGS. 2A and 2B the elongate structure 252 is illustrated in a first position 266. In FIGS. 2C and 2D, the elongate structure 252 is illustrated in a second position 268. For ease of illustration, FIGS. 2B and 2D illustrate the elongate structure 252 separated from the elongate body 224 of the positioning device 222.

In the first position 266 (e.g., FIGS. 2A and 2B), the elongate structure 252 is extendably positioned within the first lumen 234, the channel 246, and the third lumen 248 of the elongate body 224, as discussed herein. In the second position 268 (e.g., FIGS. 2C and 2D), the elongate structure 252 extends away from the channel 246. In addition, the second position 268 also illustrates the predetermined bend at the flexible portion 264, as well as the rotation of the elongate structure along the rotation point 260. As shown in FIG. 2C, a portion of the elongate structure 252 proximal to and at the distal end 256 is rotated substantially 90 degrees relative to the elongate body 224. As will be discussed herein, rotating the elongate structure substantially 90 degrees positions a piercing member substantially perpendicular to the thick tissue (i.e., septum secundum). However, in various embodiments, the elongate structure 252 can be rotated more than 90 degrees and less than 90 degrees.

In one embodiment, the movement from the first position 266 to the second position 268 can result from a compression force, indicated by arrow 262 in FIG. 2B, applied to the elongate structure 252. As used herein, the compression force is a force applied through the elongate structure 252 to impart compression on the rotation point 260 of the elongate structure 252. The compression force can originate from the proximal end 254 of the elongate structure 252 by a pushing force applied to the elongate structure at the proximal end 254 of the elongate structure 252.

To move from the first position 266, as shown in FIG. 2B, to the second position 268, as shown in FIG. 2D, the pushing force can be applied by a deployment shaft, as will be discussed herein, towards the proximal end 254 of the elongate structure 252. Pushing force applied to the deployment shaft acts on the pivots of the rotation point 260. As the compression force increases, a result of increasing the pushing force at the proximal end 254, a column strength of the elongate structure is eventually overcome such that the flexible portion 264 of the elongate structure 252 begins to bend relative the remainder of the elongate structure 252. As the flexible portion 264 begins to bend, the elongate structure 252 begins to extend away from the channel 246 of the elongate body 224. As the elongate structure 252 extends away, the predetermined bend of the flexible portion 264 begins to form as the distal end 256 of the elongate structure 252 rotates along the rotation point 260 of the elongate structure 252 to the second position 268.

At the second position 268, the distal end of the elongate structure is positioned substantially 90 degrees relative to the elongate body 224 and is temporarily locked in the second position 268. Locking the elongate structure in the second position 268 can include a number of methods and/or mechanisms. In one embodiment, for example, the deployment shaft used to apply the pushing force can be locked to prevent it from backing away from the elongate structure, and thus releasing the pushing force acting on the elongate structure.

To move from the second position 268 to the first position 266, a pulling force can be applied to the proximal end 254 of the elongate structure 252 to pull the elongate structure 252 from the second position 268 to the first position 266. For example, in some embodiments, the pulling force can be the result of pulling the proximal end 254 of the elongate structure 252 with the deployment shaft or directing grasping and pulling the proximal end 254 of the elongate structure 252, as will also be discussed herein.

FIGS. 2E through 2I illustrate various embodiments of a piercing member 270 and a fastening member 272 according to the teachings of the present disclosure. In various embodiments of FIGS. 2E-2H, the piercing member 270 can be slidably positioned within the lumen 258 of the elongate structure 252. In such embodiments, the piercing member is positioned proximal the distal end 256 of the elongate structure 252, as shown in FIGS. 2A and 2B. In various embodiments, piercing member 270 can be moved within the lumen 258 of the elongate structure 252 such that a portion of the piercing member 270 moves through the wall opening 250 and away from the wall 230, as shown in FIGS. 2C and 2D.

In various embodiments of FIGS. 2E-2I, the fastening member 272 can be releasably positioned within a lumen 274 of the piercing member. As will be discussed in more detail in FIGS. 4A-4C, the piercing member 270 can be moved within the lumen 258 of the elongate structure 252 and through the wall opening 250 using a deployment shaft to pierce thick and/or thin tissue (SS and SP) of the passage. In such embodiment, the fastening member 272 releasably positioned within the lumen 274 of the piercing member 270 can be released from the piercing member 270 to fasten thick and thin tissue of the passage together to seal a patent foramen ovale.

Figure 2E:
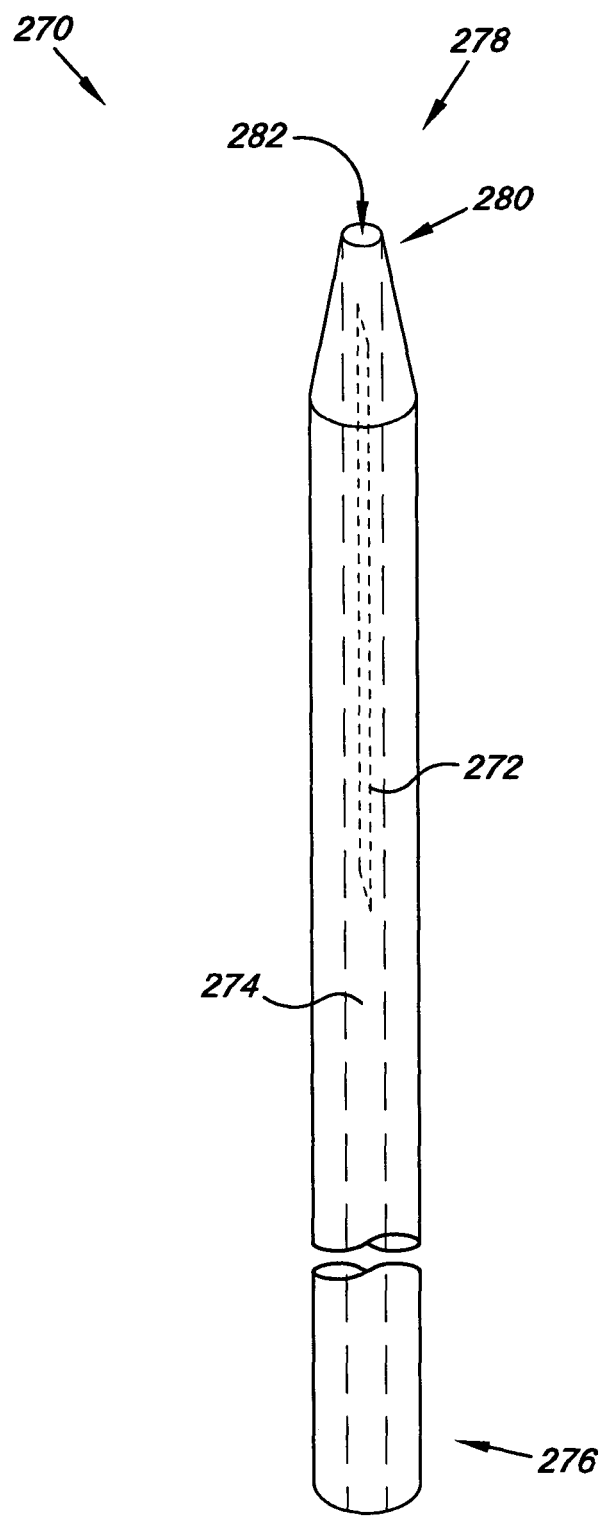
FIG. 2E illustrates a piercing member of the positioning device according to one embodiment of the present invention.

Referring now to FIG. 2E, piercing member 270 includes an elongate body having a proximal end 276 and a distal end 278. As shown in FIG. 2E, the distal end 278 includes surfaces that define a piercing structure 280 and an opening 282. As shown in FIG. 2E, the piercing structure 280 includes a pointed tip that allows the piercing member 270 to pierce the thick tissue (SS) and the thin tissue (SP). In addition, the piercing member 280 includes the opening 282 that allows the fastening member 272 to be released from the piercing member 270. In an alternative embodiment, the piercing structure 280 can include a pointed cap formed of a bioabsorbable material and releasably coupled to the pointed structure over opening 282. In such an embodiment, the pointed cap can aid in the piercing of tissue by the piercing member and help to prevent tissue and debris from entering the lumen of the piercing member prior to the release of the fastening member 272. In this embodiment, the pointed cap could be released from the piercing member by a pushing force exerted on the cap by the fastening member 272 and dissolved within the body.

FIGS. 2F-2I illustrates various embodiments of the fastening member 272. In various embodiments of FIGS. 2F-2I, the fastening member 272 includes an elongate body 284 having a first end 286 and a second end 288 that can include various structures and surfaces that preclude thick and thin tissue of the passage of a PFO from moving away from so as to occlude the PFO, as will be discussed below with respect to FIGS. 5A-5G.

In various embodiments of FIGS. 2F-2I, the elongate body 284 of the fastening member 272 includes a base portion 290. The base portion 290 can include various lengths and widths. The length and width of the base portion 290 can depend on the type and configuration of the fastening member 272, as well as the anatomical dimensions of the thick and thin tissue to which the fastening member 272 fastens. As will be discussed below, the base portion 290 serves to anchor the first and second ends 286 and 288 to the elongate body 284 and to add strength and support to the elongate body 284 of the fastening member 272.

As discussed above, in various embodiments, the elongate body 284 of the fastening member 272 can be formed from shape memory polymers and from alloys having shape memory, super elastic, and/or linear elastic properties. For example, in various embodiments, the fastening member 272 can be formed from a Nitinol alloy. In various embodiments, the Nitinol alloy can include super elastic, non-super elastic (linear elastic), and/or shape memory alloys that may also include other minor amounts of other metals to achieve desired properties, e.g., strengthened first and second ends 286 and 288 and/or base portion 290. In addition, the fastening members may include various layers of these alloys to provide varying characteristics and properties to the fastening member 272. For example, in various embodiments, the fastening member 272 can include a first layer having a core formed of a super elastic Nitinol alloy, and a second layer covering the core and formed of a linear elastic Nitinol alloy. In some embodiments, the first and second ends 286 and 288 can be formed of a shape memory metal having a higher concentration of iron or stainless steel relative to the base portion 290 of the elongate body 284 to increase the strength of the first and second ends 286 and 288. Other materials and configurations are also possible.

In some embodiments of FIGS. 2F-2I, the fastening member can be formed entirely of a flexible bioabsorbable material. In such embodiments, the fastening member can fasten thick and thin tissue In various embodiments of FIGS. 2F-2I, the elongate body can be configured so as to have the ability to move radially between a collapsed state 292 and an expanded state 294. In various embodiments, the fastening member 272 may have an elongated collapsed configuration where the fastening member 272 is stretched and compressed along its longitudinal axis, as for example, when positioned within the lumen 274 of the piercing member 270 (e.g., FIG. 2E). In the expanded state 294, the fastening member 272 forms a predefined shape. The predefined shape can function to fasten thick tissue to thin tissue and vice versa so as to hold the tissue together and occlude a PFO. For example, in various embodiments, the fastening member can include a generally linear shape in the collapsed state. In the expanded state, the fastening member can include helical shapes, vortex shapes, crescent shapes, curved shapes, saddle shapes, and irregular shapes. In various embodiments, these predefined shapes can include surfaces and structures that help to engage thick and thin tissue of the passage. As used herein, engaging thick and thin tissue can include piercing, trapping, clamping, grasping, gripping, hooking, abutting, catching, pushing, and pulling thick and thin tissue of the passage to fasten the tissue and occlude a PFO.

As will be discussed herein with respect to FIGS. 5A-5G, the thick and thin tissue of the passage will have a tendency to move away from each other once the tissues are fastened. To counter this tendency, the base portion 290 can function to anchor the first and second ends 286 and 288 to the elongate body 284 and thereby substantially preclude the thick and thin tissue from moving away from each other once the first and/or second ends have engaged the thick and thin tissue. In addition, in various embodiments, the base portion 290 and the first and second ends 286 and 288 of the fastening member 272 can include a number of engaging mechanisms and structures, such as barbs, pointed tips, and surfaces for engaging thick and thin tissue of the passage. For example, in various embodiments, the base portion can include a barb structure to engage tissue and preclude tissue from backing away from each other as the fastening member is being positioned. This functionality and others will be described below in more detail in FIGS. 5A-5G.

Figure 2F:
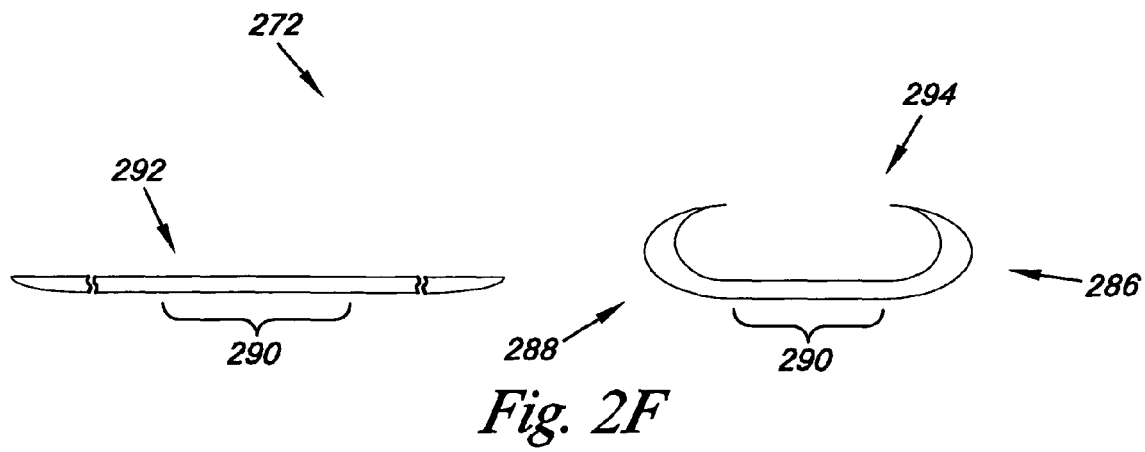
FIGS. 2F-2I illustrate various embodiments of a fastening member of the positioning device according to the teachings of the present invention.

Referring now to the embodiment illustrated in FIG. 2F, the fastening member 272 includes the collapsed state 292 and an expanded state 294. As discussed above, in the collapsed state, the fastening member 272 is generally elongated along its longitudinal axis, a result of having shape memory properties, linear elastic properties and/or super elastic properties that allow the fastening member to retain its shape within a lumen of a component of the positioning device or through compressive forces acting on the fastening member by surfaces of the lumen of the component. In the expanded state 294, the fastening member 272 illustrated in FIG. 2F relaxes to a predefined shape that resembles a crescent shape having pointed tips at the first and second ends 284 and 286. In various embodiments of FIG. 2F, the pointed tips can engage thick and thin tissue to fasten the tissue.

Figure 2G:
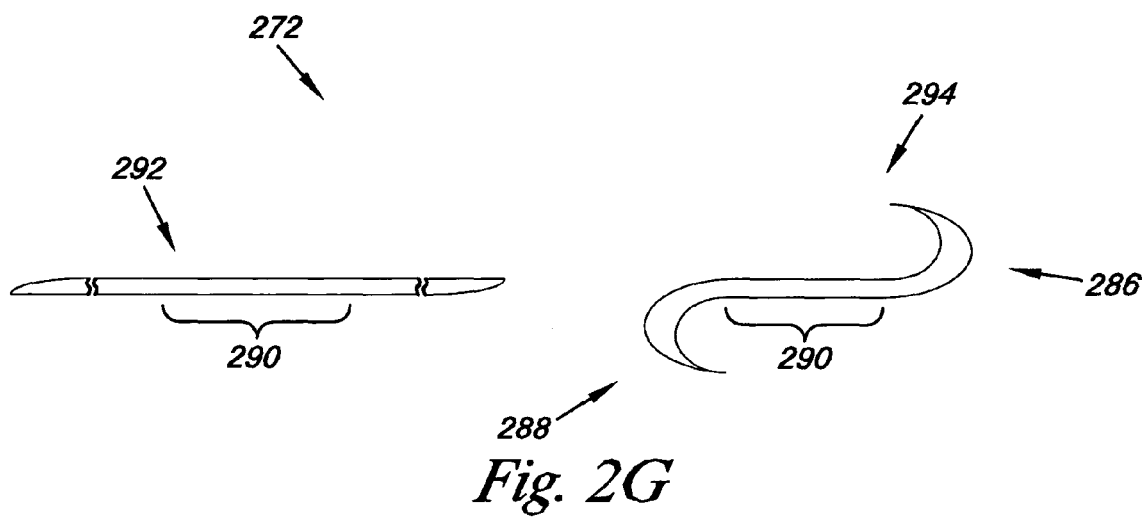

FIG. 2G illustrates another embodiment of the fastening member 272. As shown in FIG. 2G, the fastening member includes the collapsed and expanded state 292 and 294. In the expanded state 294, the fastening member 272 includes an S-shape having pointed tips at the first and second ends 284 and 286 that can engage thick and thin tissue to fasten the tissue.

Figure 2H:
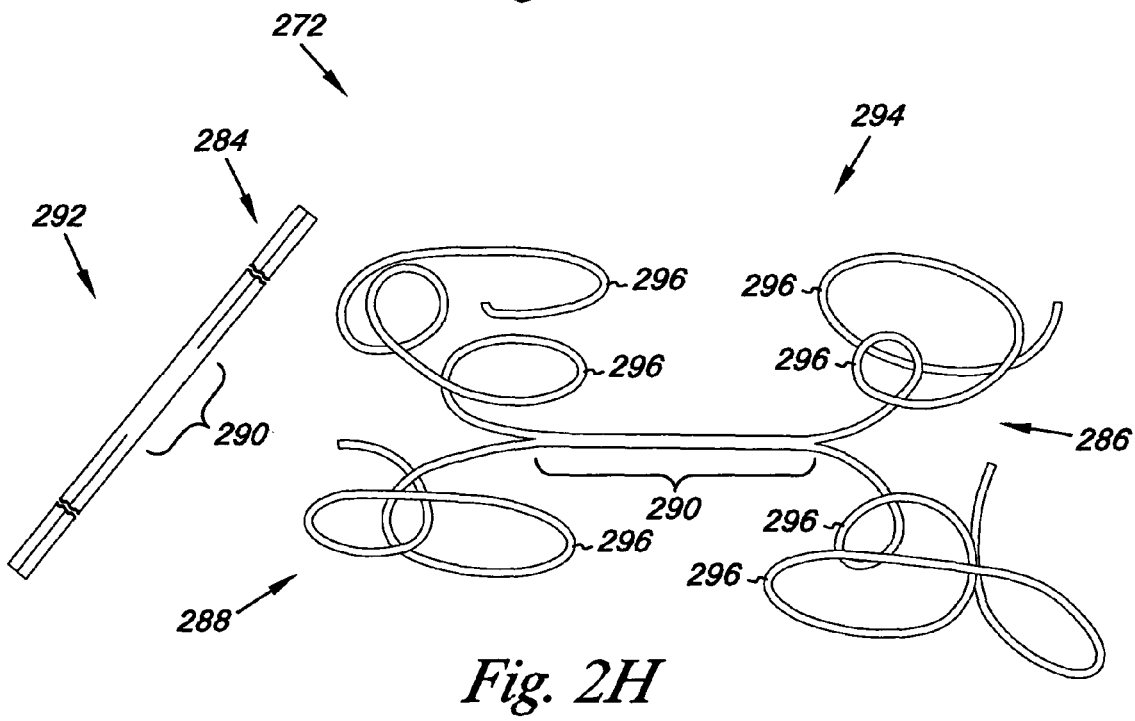

FIG. 2H illustrates another embodiment of the fastening member 272. As shown in FIG. 2H, the fastening member 272 includes an expanded state 294 having first and second ends 286 and 288 that diverge from the base portion 290 to form an irregular convoluted shape. In this embodiment, various surfaces 296 of the first and second ends 286 and 288 can abut thick and thin tissue of the passage so as to preclude the tissue from moving away from each other, and thus, fasten the tissue.

Figure 2I:
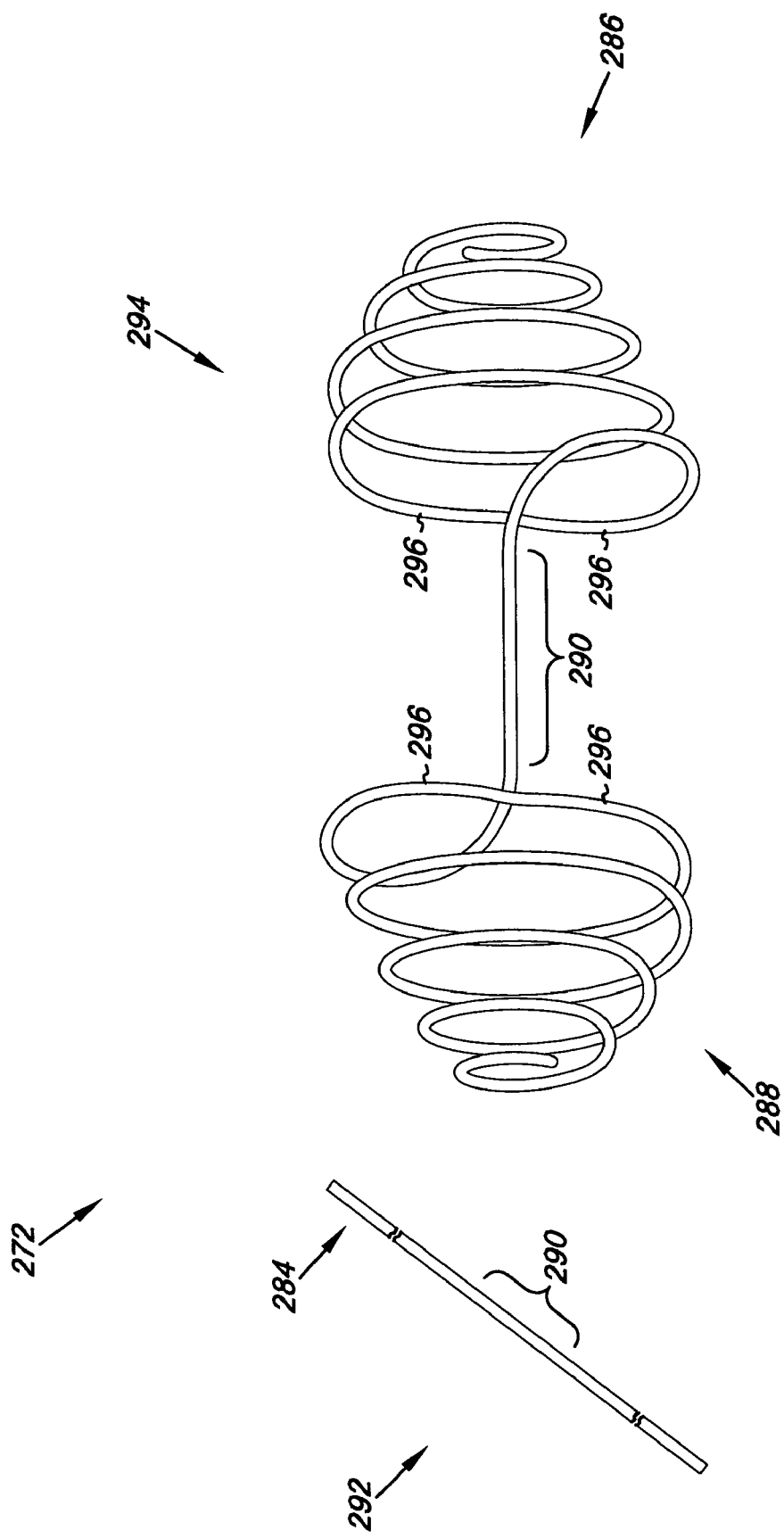

FIG. 2I illustrates another embodiment of the fastening member 272. As shown in FIG. 2I, the fastening member 272 includes an expanded state 294 having first and second ends 286 and 288 that form a helical shape. In this embodiment, surfaces 296 of the first and second ends 286 and 288 can abut thick and thin tissue of the passage so as to preclude the tissue from moving away from each other, and thus, fasten the tissue.

As will be discussed below with respect to FIGS. 5A-5G, surfaces 296 proximal to the base support 290 will abut the thick and thin tissue as opposed to surfaces distal to the base portion. In various embodiments, the first and second ends 286 and 288 can include barbs, and other structures that can engage thick and thin tissue of the passage. For example, in various embodiments, surfaces 296 can include barbs or pointed projections.

Figure 4C:
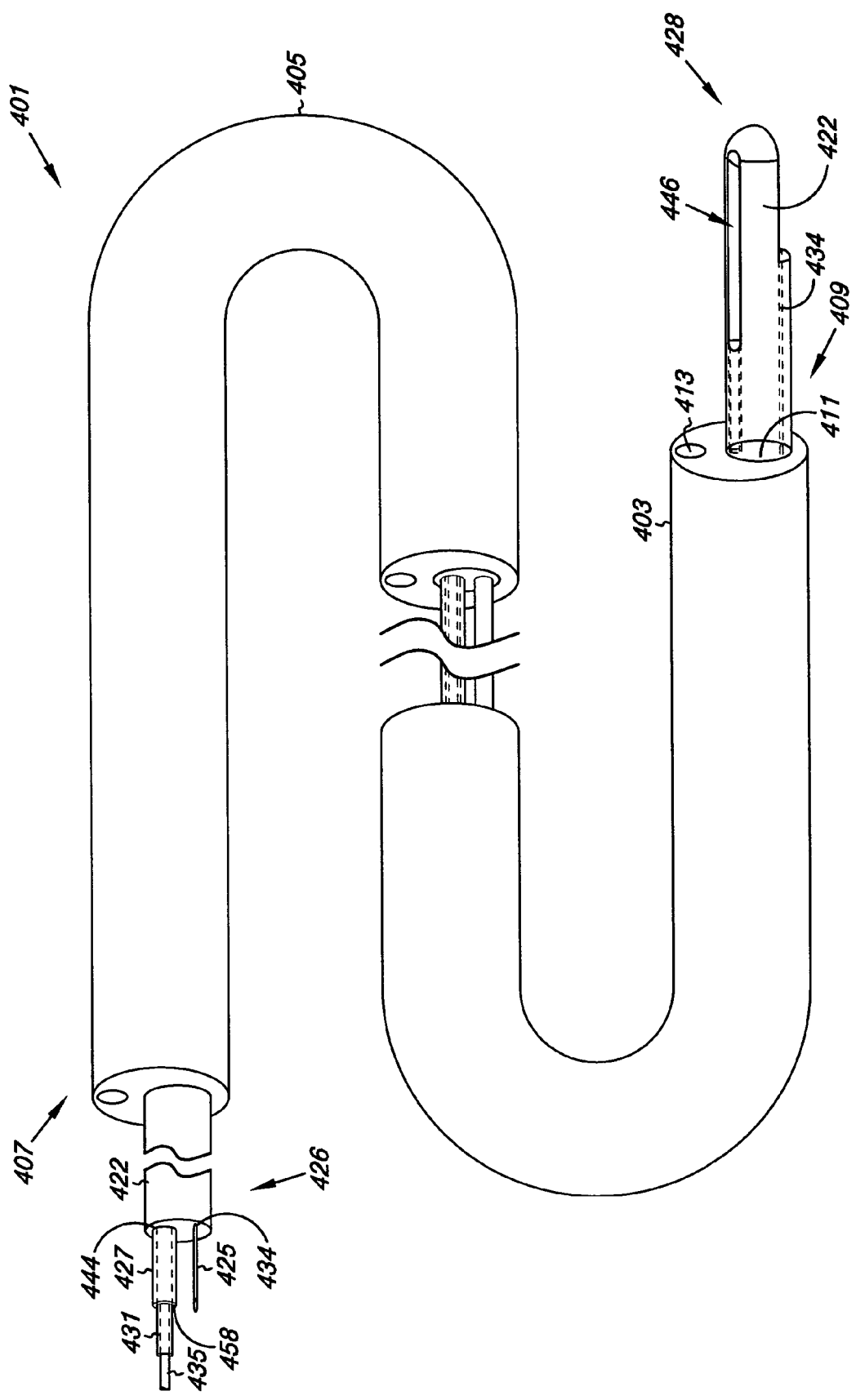

FIGS. 4A-4C illustrate various embodiments of a system 401 that includes the positioning device 422 of the present invention. As shown in FIGS. 4A and 4B, system 401 includes positioning device 422, as described herein. System 401 also includes a catheter 403. The catheter 403 includes an elongate body 405 having a proximal end 407 and a distal end 409. In various embodiments, the positioning device 422 can be located between the proximal end 407 and the distal end 409 of the catheter 403. The catheter 403 includes lumen 411. In various embodiments, the lumen 411 can extend longitudinally toward the distal end 409 of the catheter 403. In one embodiment, lumen 411 extends from the proximal end 407 to the distal end 409 of the catheter 403.

The catheter 403 can further include a guidewire lumen 413. The guidewire lumen 413 can extend within the elongate body 405 of the catheter 403 from the proximal end 407 to the distal end 409 of the catheter 403. In various embodiments, the guidewire lumen 413 can receive a guidewire for positioning the catheter 403 and the positioning device 422 within a heart chamber (e.g., a right atrium of a patient).

In various embodiments, the system 401 can include a sheath 415 having proximal end 417 and a distal end 419. In some embodiments, the sheath 415 can be slidably positioned within the lumen 411 of the catheter 403. In one embodiment, the positioning device 422 can be coupled to the sheath 415 at the distal end 419 of the sheath 415. In such an embodiment, the sheath 415, including the positioning device 422 coupled thereon, can be slidably positioned within the lumen 411 of the catheter 403 to deploy the positioning device 422 from the catheter 403. In some embodiments, the positioning device can be slidably positioned within the lumen of the catheter without the sheath, as will be discussed below with respect to FIG. 4C.

The sheath 415 includes a number of lumens extending between the proximal end 417 and the distal end 419 of the sheath 415. As shown in FIGS. 4A and 4B, the sheath 415 includes a first lumen 421 and a second lumen 423. In various embodiments, the catheter and the sheath can include various lumen designs, e.g., coaxial, dual, triple, quadruple, etc., lumen designs. In the embodiment shown in FIGS. 4A and B, the catheter 403 includes a dual lumen design (e.g., lumen 411 and guidewire lumen 413) and the sheath 415 includes both a dual lumen design (e.g., first lumen 421 and second lumen 423) and a coaxial lumen design (e.g., third lumen 429 within second lumen 423).

In various embodiments, the first and second lumens 421 and 423 of sheath 415 can house various components of the system 401 that move within the first and second lumens 421 and 423. For example, the system 401 can include a number of deployment shafts positioned within the first and second lumens 421 and 423. The deployment shafts can be used to deploy the various components (e.g., the elongate structure 252 shown in FIGS. 2A-2D) of the positioning device 422 from the catheter 403. In one embodiment, the first lumen 421 of the sheath 415 includes a first deployment shaft 425 therein. The first deployment shaft 425 can be positioned adjacent the base of the extension member, as discussed herein. In such embodiments, the first deployment shaft 425 moves within the first lumen 421 of the sheath 415 and the first lumen of the elongate body 424 to extend (i.e., push) the extension member from the first lumen of the elongate body 424 of the positioning device 422.

The second lumen 423 of the sheath 415 includes a second deployment shaft 427 positioned therein. In various embodiments, the second deployment shaft 427 can be positioned adjacent the proximal end of the elongate structure, as discussed herein. In such embodiments, the second deployment shaft 427 moves within the second lumen 423 of the sheath 415 and the second lumen of the elongate body of the positioning device 422 to extend the elongate structure away from the channel 446 of the elongate body 424, as discussed herein.

The sheath 415 can also include a third lumen 429. The third lumen 429 can include a third deployment shaft 431 positioned therein. In various embodiments, the third deployment shaft 431 can be positioned adjacent the piercing member, as discussed herein. In such an embodiment, the third deployment shaft 431 moves within the third lumen 429 of the sheath 415 and the lumen of the elongate structure to push the piercing member from the lumen of the elongate structure, as discussed herein.

The sheath 415 can include a fourth lumen 433. The fourth lumen 433 can include a fourth deployment shaft 435 positioned therein. In various embodiments, the fourth deployment shaft 435 can be positioned adjacent the releasably positioned fastening member, as discussed herein. In such an embodiment, the fourth deployment shaft 435 moves within the fourth lumen 433 of the sheath 415, the lumen of the elongate structure and the lumen of the piercing member to release the fastening member from the lumen of the piercing member, as discussed herein.

In various embodiments of the present disclosure, a targeting device 437 can be implemented to help locate various anatomical structures within the human body, e.g., the thick and thin tissue of the passage of a PFO. The targeting device 437 can also be used to help guide, direct, manipulate, etc., the positioning device and various components of the positioning device to a target in the human body. As used herein, a target is a location to be treated with the positioning device, for example, a patent foramen ovale (PFO). As used herein, creating and/or locating a target means visually defining a target using a display screen, e.g., 439, to display an image of the target on the display screen 439. In some embodiments, creating and/or locating a target can involve the use of program instructions executing on a computer 441 to define a target. In various embodiments, program instructions can include, among other things, various algorithms such as trigonometric algorithms (e.g., triangulation), dynamic depth focusing algorithms, etc. that can help to locate, define, and/ or guide an operator of the positioning device to the target and manipulate the target using the positioning device 422 and components of the positioning device 422.

The targeting device 437 can include a single component or multiple components. In various embodiments, the components of the targeting device 437 can be located at a target, proximal to a target, and/or distal to the target. For example, in some embodiments, the targeting device 437 can include multiple components where one component is located adjacent the target, and another component is located distal to the target. For example, in various embodiments, the targeting device can include radiopaque markers as one component of the targeting device located adjacent the target. The radiopaque markers can be coupled to the catheter, the positioning device, and/or various components of the positioning device, e.g., piercing member and/or fastening member. As another component, the targeting device 437 can include the display screen 439 located distal to the target (i.e., outside the human body) to provide an image of the radiopaque markers at or proximal to the target to verify proper position, among other things, of the catheter, positioning device, and/or components of the positioning device.

Examples of the targeting device 437 and components of the targeting device 437 can include, but are not limited to, imaging probes and devices (e.g., magnetic resonance imaging, ultrasound imaging, optical imaging), Doppler devices (e.g., Doppler audio), software, computers, dynamic depth focusing devices, targeting markers (e.g., ultrasound targeting icons, radiopaque markers), etc. Other devices and components of the targeting device can include echogenic, angioscopic, and fluoroscopic visualization techniques. In some embodiments, the targeting device 437 can include Virtual Reality (VR) systems, and Augmented Reality Systems, where real-time information, such as an image of a PFO from the patient, is integrated with that from a 3-D model of the patient's PFO from a Virtual Reality system. Other visualization devices and systems are also contemplated.

In various embodiments, the targeting device can provide real-time images of the target (e.g., via a real-time imaging ultrasound device, a real-time MR imaging device, a real time optical imaging device, etc.). The real-time images can be provided before, during, and/or after the application of energy to the target. For example, in various embodiments, the targeting device 437 can include a real-time imaging ultrasound device configured to provide real-time images of a target, e.g., PFO, such that an operator of the positioning device can guide the positioning device to the target, and manipulate the target with components of the positioning device while simultaneously viewing the target in real time.

FIG. 4C illustrates another embodiment of system 401. In the embodiment illustrated in FIG. 4C, the positioning device 422 is slidably positioned within the lumen 411 of the catheter 403 without the sheath. In this embodiment, the catheter includes a dual lumen design and the positioning device includes lumens having both a dual lumen design and a coaxial lumen design. As shown in FIG. 4C, the proximal end 426 of the positioning device 422 can extend from lumen 411 at the proximal end 407 of the catheter 403. In the embodiment illustrated in FIG. 4C, the positioning device 422 can be deployed from the distal end 409 of the catheter 403 by applying a pushing force to the proximal end 426 of the positioning device 422.

The embodiment illustrated in FIG. 4C can include a number of deployment shafts, as discussed herein. The deployment shafts can extend within the various lumens of the elongate body 424 of the positioning device 422 to deploy the various components of the positioning device 422. For example, the first deployment shaft 425 can be positioned within the first lumen 434 of the elongate body 424 and adjacent the base (i.e., proximal end) of the extension member, as discussed herein. In such embodiments, the first deployment shaft 425 moves within the first lumen 434 of the elongate body 424 to push the extension member from the first lumen 434 of the elongate body 424 and through the ledge opening, such that the extension member extend away from the ledge 432 of the positioning device 422, as discussed herein with respect to FIGS. 2A-2D.

Additionally, the second deployment shaft 427 can be positioned adjacent the proximal end of the elongate structure, as discussed herein. In such embodiments, the second deployment shaft 427 moves within the second lumen 444 of the elongate body 424 to extend the elongate structure away from the channel 446, as discussed herein with respect to FIGS. 2A-2D.

The third deployment shaft 431 can be positioned within the lumen 458 of the elongate structure and adjacent the slidably positioned piercing member, as discussed herein. In such embodiments, the third deployment shaft 431 moves within the lumen 458 of the elongate structure to move a portion of the piercing member through the wall opening and away from the wall of the positioning device, as discussed herein with respect to FIGS. 2A-2E.

The fourth deployment shaft 435 can be positioned within the lumen 458 of the elongate structure, the lumen of the piercing member and adjacent the releasably positioned fastening member, as discussed herein with respect to FIG. 2E.

In such an embodiment, the fourth deployment shaft 435 moves within the lumen of the elongate structure and the lumen of the piercing member to release the fastening member from the lumen of the piercing member.

In an alternative embodiment, some components of the positioning device do not include deployment shafts for their deployment. In such an embodiment, various components of the positioning device can be deployed from the elongate body of the positioning device by manipulating the components themselves. For example, the extension member and the elongate structure can include proximal ends that extend out of the positioning device at the proximal end of the positioning device. In this configuration, a surgeon can apply a pushing force to the proximal end of the extension member, for example, to extend the extension member away from the ledge of the positioning device, as discussed herein. In various embodiments of FIG. 4C, system 401 can include the targeting device illustrated in FIGS. 4A and 4B.

The embodiments of the present invention further include methods for forming the positioning device of the present invention, as discussed herein. For example, the elongate body of the positioning device can be formed from a plastic and/or metal or metal alloy. In various embodiments, the wall can be formed to extend from the distal end toward the proximal end. A ledge can be formed to extend away from the wall. In various embodiments, the ledge can extend away from the wall perpendicularly or at other angles. In various embodiments, the ledge can be formed to include a surface that defines the first opening. Similarly, the wall can be formed to include a surface that defines a ledge opening.

In various embodiments, the elongate body of the positioning device can be formed to include the first lumen, the second lumen, the channel, and the third lumen. In such embodiments, the second lumen can extend toward the distal end of the elongate body. In one embodiment, the second lumen extends between the proximal end of the elongate body and the channel.

In various embodiments, surfaces of the elongate body can be formed in such a way as to define the channel. In various embodiments, the channel can be formed to extend longitudinally between the second lumen and the third lumen. The third lumen can be formed such that it extends from the wall opening and through the elongate body. In such embodiments, the third lumen is in communication with the channel.

In various embodiments, the first lumen, the channel, and the third lumen can formed to include a contiguous conduit in which components of the positioning device can be positioned, extended, and/or retracted.

Forming the components of the positioning device can include forming the extension member such that it is extendably positioned within the first lumen toward the distal end of the positioning device. Forming the extension member can include positioning the extension member in the compressed state within the first lumen of the elongate body. Additionally, the elongate structure can be formed such that it is extendably positioned within the second lumen toward the distal end of the positioning device. The elongate structure can be formed to include a lumen that extends between the proximal end and the distal end of the elongate structure. In various embodiments, the piercing member can be formed such that it is releasably positioned within the lumen of the elongate structure proximal the distal end of the elongate structure. In various embodiments, forming the piercing member can include forming a lumen within the piercing member and an opening in communication with the lumen. In such embodiments, the method can include forming a fastening member and releasably positioning the fastening member within the lumen of the piercing member.

Various embodiments of the positioning device described herein may be used to occlude a patent foramen ovale. For example, embodiments of the present invention can include methods to pierce tissue of the septum secundum (SS) and the septum primum (SP) and to occlude (i.e., seal) the passage of a patent foramen ovale (PFO) defined by the tissue of the SS and the SP.

FIGS. 5A-5F illustrate various method embodiments that can be implemented to occlude a PFO. These method embodiments describe how to seat the positioning device described herein on the limbus of the SS. In addition, these method embodiments describe how to locate and manipulate the various components of the positioning device described herein for piercing and occluding.

Figure 5A:
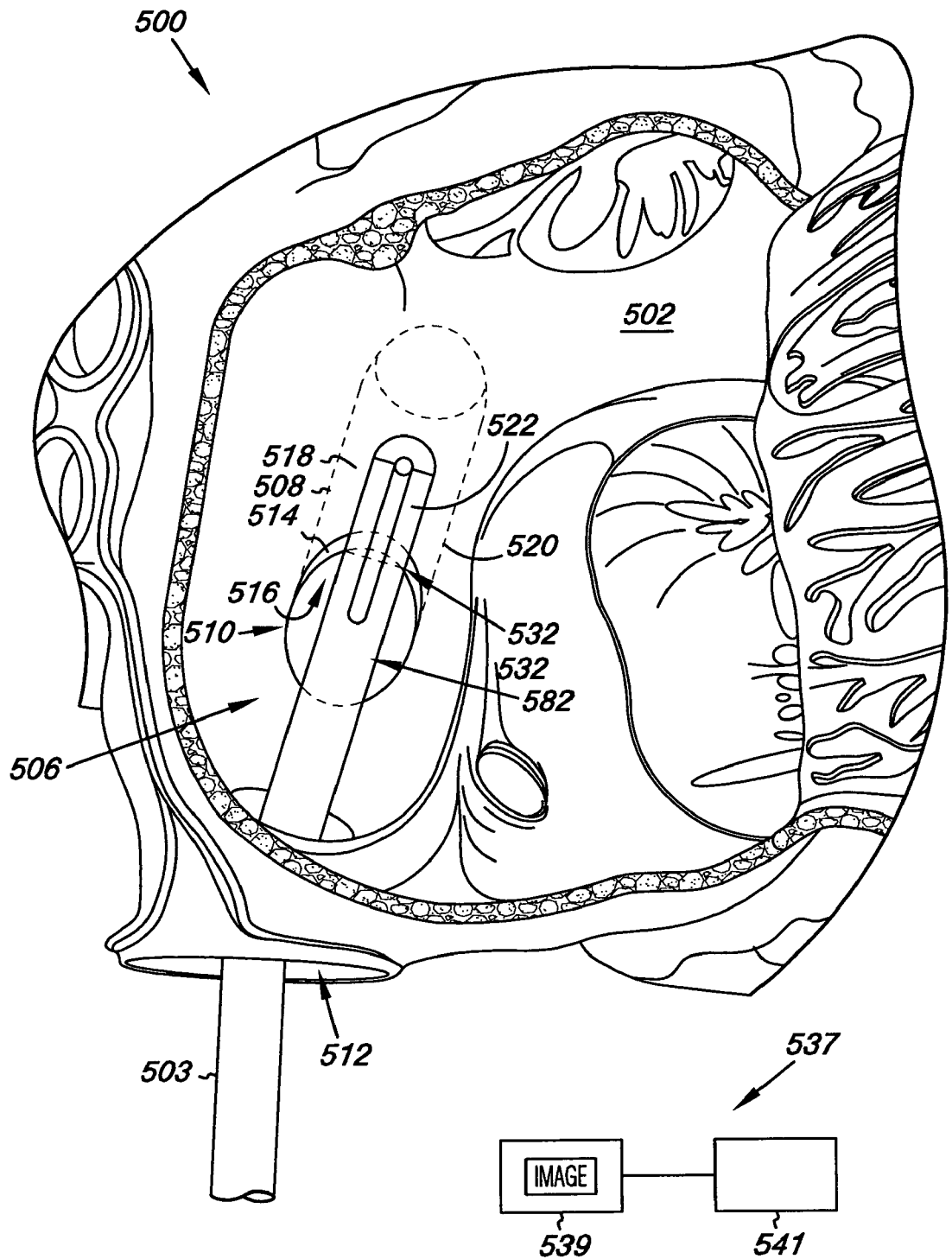
FIG. 5A illustrates the system within the right atrium of the heart according to an embodiment of the present invention.
Figure 5B:
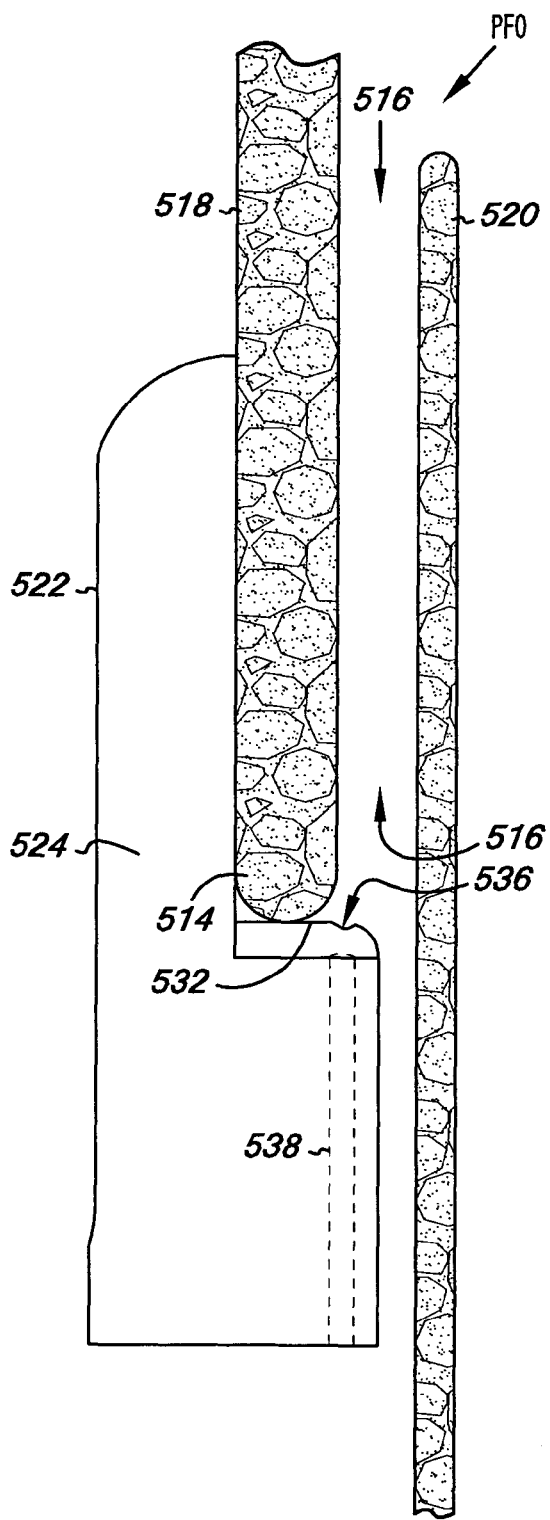
FIGS. 5B-5C illustrate the positioning device seated on the limbus of the septum secundum according to the teachings of the present invention.
Figure 5C:
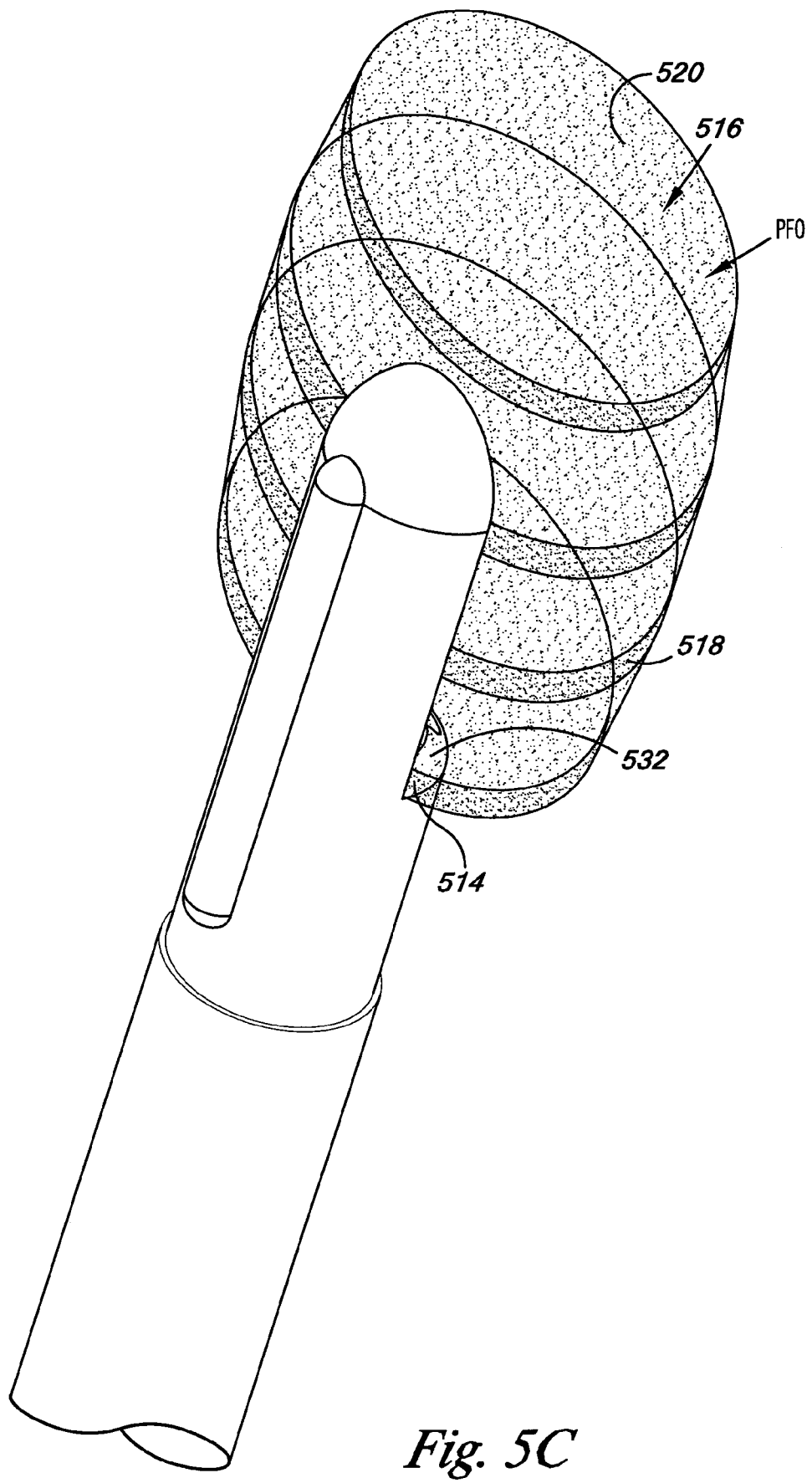
Figure 5D:
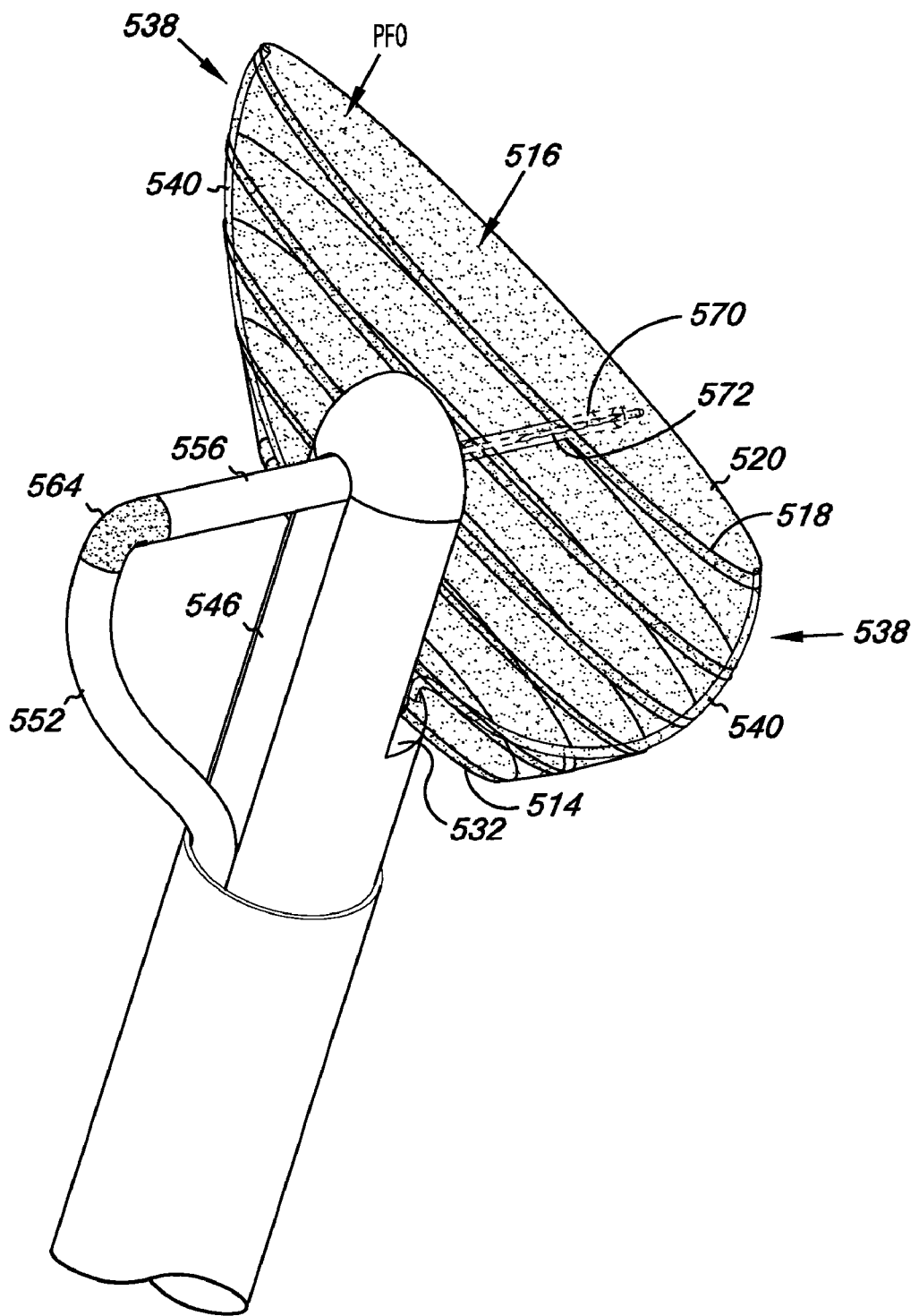
FIG. 5D provides an illustration of tightening the tissue defining the passage according to the teachings of the present invention.
Figure 5E:
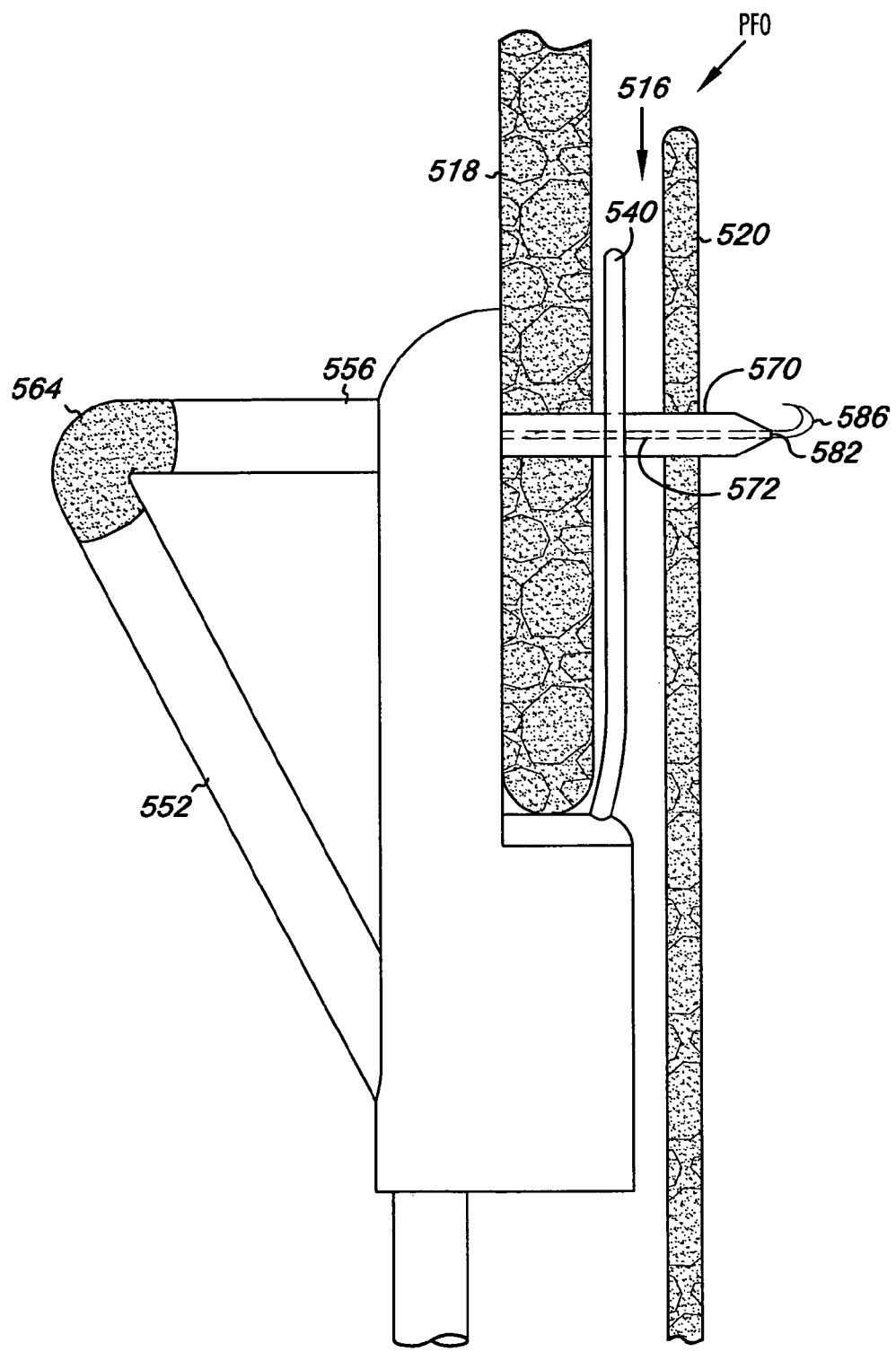
FIG. 5E provides an illustration of piercing the thick and thin tissue and of the passage according to the teachings of the present invention.
Figure 5F:
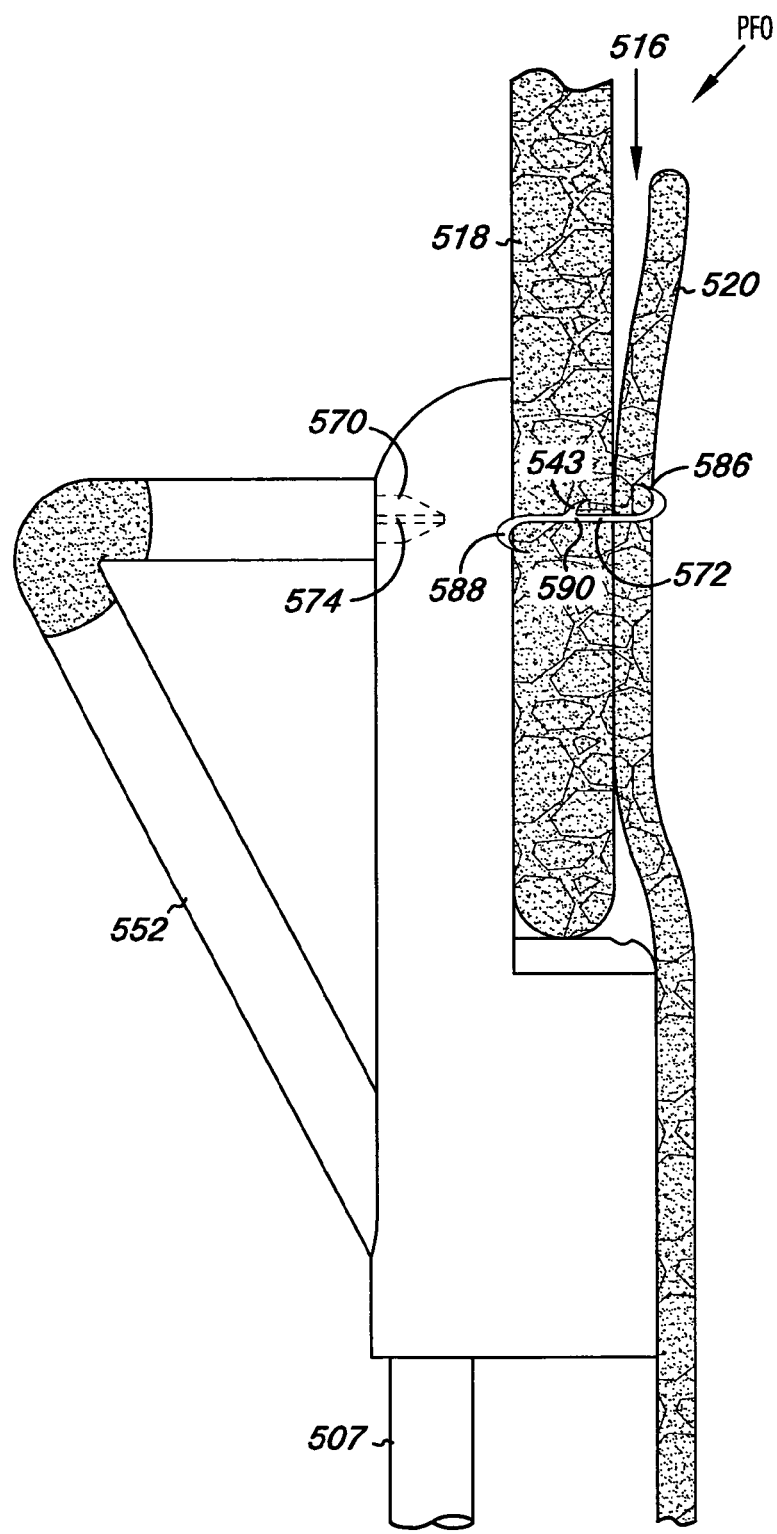
FIG. 5F provides an illustration of fastening the thick and thin tissue of the passage according to the teachings of the present invention.

FIG. 5A provides an illustration of accessing the right atrium 502 of the heart 500 according to the present invention. FIGS. 5B-5C provide illustrations of seating the positioning device 522 on the limbus 514 of the SS (thick tissue 518) according to the present invention. FIG. 5D provides an illustration of tightening the tissue defining the passage 516 according to the present invention. FIG. 5E provides an illustration of piercing the thick and thin tissue 518 and 520 of the passage 516 according to the present invention. FIG. 5F provides an illustration of bringing tissue of the passage 516 together and releasing the fastening member 572 from the piercing member 570. Finally, FIG. 5G provides an illustration of an occluded or sealed passage 516 (i.e., occluded patent foramen ovale).

Figure 5G:
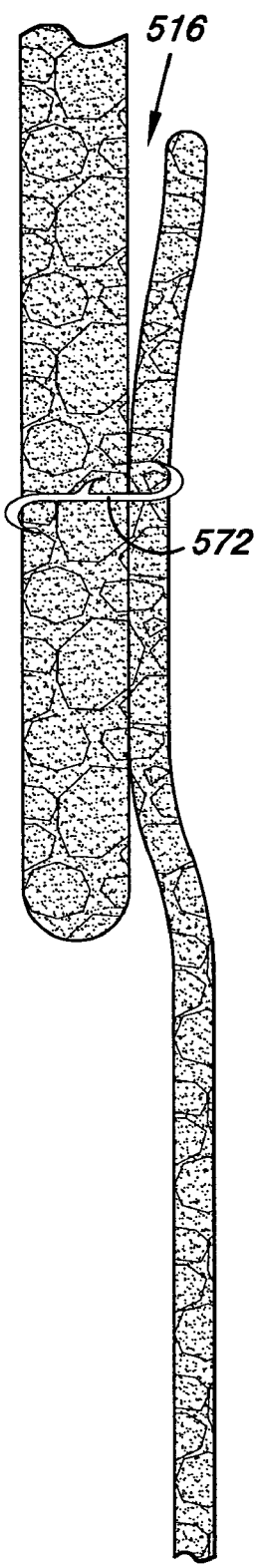
FIG. 5G provides an illustration of an occluded PFO.

As the reader will appreciate, tightening tissue of the passage, as shown in FIG. 5D, can be implemented prior to piercing and occluding the passage, as shown in FIGS. 5E and 5G. However, in some embodiments, the passage can be pierced and occluded without tightening the tissue of the passage.

The embodiments illustrated in FIGS. 5C and 5D show the passage 516 (i.e., the patent foramen ovale), among other things. For purposes of simplicity however, the PFO, illustrated in FIGS. 5C and 5D, includes dark bands on the upper portion, e.g., rightward portion, of the passage, which are labeled as 518. The dark bands are intended to illustrate that the upper, e.g., rightward, portion of the passage 516 is formed substantially of thick tissue 518 and the lower, leftward, portion of the passage 516 is formed of substantially thin tissue 520, as discussed herein.

In addition, the passage 516 illustrated in FIGS. 5C and 5D is intended to show, generally, a change in the shape of the passage 516. As discussed herein, the change in the shape of the passage 516 is the result of the arms 540 of the extension member 538 extending away from the ledge 532 so as to create the expansion force on the inner surfaces of the tissue, as discussed herein.

Referring now to FIG. 5A, the method for positioning the positioning device 522 within the right atrium 502 includes introducing the catheter 503 into the venous system of the patient using a minimally invasive percutaneous, transluminal catheter based delivery system.

A unique aspect of the passage 516 is its location relative to the orifice of the inferior vena cava 512. Since the passage 516 is located above and to the left of the orifice of the inferior vena cava 512, the positioning device 522 can be deployed upon entering the right atrium 502 from the orifice of the inferior vena cava 512. For example, a guidewire can be positioned within the venous system and advanced to the right atrium 502 of a patient. In one embodiment, the right atrium 502 can be entered via the orifice of the inferior vena cava 512. The catheter 503, including the positioning device 522, as described herein, can be positioned over the guidewire and the catheter advanced so as to position the distal end 582 of the catheter 503 at or adjacent the septal wall 506 of right atrium 502. Once positioned within the right atrium 502, the positioning device 522 can be deployed from the catheter 503.

In various embodiments, components of the targeting device 537, such as computer 541 executing program instructions thereon, display 539, and radiopaque markers on the catheter 503 and/or the positioning device 522 can be used to help position the positioning device 522 within the right atrium 502 and/or to seat the positioning device 522 on the limbus 514, as will be discussed herein. In addition, orientation and visualization of the positioning device 522 and the various components of the positioning device (e.g., elongate structure, piercing member, fastening member, and extension member) may be accomplished through the use of any combination of targeting device components such as echogenic, angioscopic, ultrasound, MRI, and fluoroscopic visualization techniques, among others as described herein.

Referring now to FIGS. 5A-5C, seating the positioning device 522 on the limbus 514 of the SS 518 can include positioning the elongate body 524 adjacent the limbus 514 of the SS 518. To do this, the deployed positioning device 522 can be positioned against the septal wall 506 and slid along the septal wall 506 of the right atrium toward the interatrial septum 508. Because the limbus 514 includes the pronounced anterosuperior margin of the fossa ovalis 510, the limbus 514 can catch the ledge 532 of the positioning device 522 as the positioning device 522 slides along the septal wall 506 to seat the positioning device 522 on the limbus 514. Verification of proper positioning on the limbus can be performed by the targeting device 537 as described herein.

In various embodiments, seating the positioning device 522 on the limbus 514 can help to locate and properly position the various components of the positioning device 522. For example, seating the positioning device 522 on the limbus 514 of the SS 518 can include locating the extension member 538 of the positioning device 522 adjacent the passage 516 defining the PFO, as shown in FIGS. 5B and 5C. Locating the extension member 538 adjacent the passage 516 helps to properly position the ledge opening 536 of the elongate body 524 such that the extension member 538 can be extended into the passage 516 without being obstructed by the limbus 514, as shown in FIGS. 5B and 5C.

In various embodiments, the method can include extending the extension member 538 into the passage 516 of the PFO. In various embodiments, extending the extension member into the passage 516 can include tightening tissue of the passage 516, as shown in FIG. 5D. In the native state, the tissues that form the passage can include elevations and/or depressions along the length of the passage and thus, the surfaces are generally not linear along the length of the passage. In various embodiments, tightening the tissue of the passage 516 can help to provide for a substantially linear surface of the tissues of the passage 516 relative to the surfaces that are not tightened. For example, once the extension member 538 has been extended from the elongate body 524, the arms 540 extend away from the ledge 532 of the elongate body 524. When the arms 540 extend away from the ledge 532, the arms 540 contact the tissue and create an expansion force, as discussed herein, against internal surfaces of the passage 516 of the PFO. In one embodiment, the internal surfaces can include the thin tissue 520 of the passage 516. In another embodiment, the internal surfaces can include thin and thick tissue 520 and 518 of the passage 516. The expansion force acting on the internal surfaces of the passage 516 causes the tightening of the tissue of the passage so as to provide for substantially linear surfaces of the passage 516.

In various embodiments, tightening the tissue of the passage 516 can also include stretching the tissue of the passage 516 in different directions, such that the thin tissue 520 of the passage 516 is urged toward the thick tissue 518 of the passage 516, as shown in FIG. 5D. In one embodiment, urging the thin tissue 520 toward the thick tissue 518 of the passage 516 can provide for a reduced distance in which the piercing member 570 is extended from the elongate structure 552 to pierce both the thick and thin tissues 518 and 520 of the passage 516 as shown in FIGS. 5D and 5E. In addition, the extension member 538 can assure that the elongate body 524 of the positioning device 522 is correctly oriented with respect to the passage of the PFO. This positioning mechanism assures correct alignment for the piercing member 570 as it pierces the thick and thin tissue 518 and 520 of the passage 516.

In various embodiments, piercing the tissue defining the passage 516 can include positioning the elongate structure 552 of the positioning device substantially perpendicular to the thick tissue 518 of the passage 516 as shown in FIGS. 5D and 5E. Positioning the elongate structure 552 can include pushing the elongate structure 552 away from the channel 546 of the elongate body 524 using the first deployment shaft, as described herein with respect to FIGS. 4A-4C. As the elongate structure 552 is pushed away from the channel 546, the flexible portion 564 forms the predetermined bend and the distal end 556 of the elongate structure 552 rotates along the rotation point from the first position to the second position, as described herein with respect to FIGS. 2B-2D.

Positioning the elongate structure 552 substantially perpendicular to the thick and thin tissue 518 and 520 can help to properly position the piercing member 570 relative to the passage 516 such that the piercing member 570 can be pushed through the passage 516 at substantially a right angle relative to the thick and thin tissues 518 and 520 as shown in FIGS. 5D and 5E. In various embodiments, the rotation of the elongate structure 552 can rotate more than 90 degrees, and in other embodiments, the rotation of the elongate structure 552 can rotate less than 90 degrees.

In some embodiments, pushing the piercing member 570 through the thick tissue 518 and the thin tissue 520 of the passage 516 includes bringing the thick and thin tissue 518 and 520 together, as shown in FIGS. 5E and 5F. To do this, the first end 586 of fastening member 572 can be released from the piercing member 570 through opening 582. Once the first end 586 is released from the piercing member, it begins to assume its expanded state, as discussed herein with respect to FIGS. 2F-2I. In the embodiment illustrated in FIG. 5F, the fastening member 572 includes the fastening member 272 illustrated in FIG. 2G. As discussed with respect to FIG. 2G, the expanded state includes an S-shape. The first end 586 of the S-shaped fastening member 572 forms a hook like structure with a pointed tip, which can engage the thin tissue 520 of the passage 516 by piercing. Once the first end 586 has fully expanded and the thin tissue of the passage has been engaged, the piercing member 570 can be pulled back bringing the first end 586 of the fastening member 572 so as to cause the first end 586 to pull the thin tissue 520 into contact with the thick tissue 518, as shown in FIG. 5F. Once the thick and thin tissue 518 and 520 contact each other, the second end 588 can be released from the piercing member. To do this, the piercing member 570 can be pulled to cause it to retract into the positioning device 522 and thereby release the second end 588 from the lumen 574 of the piercing member 570. The second end begins to form its expanded state and engages the thick tissue 520 by piercing it with the pointed tip of the hook like structure. In its expanded state, the S-shape of the fastening member 572 occludes the PFO because the thick and thin tissue 518 and 520 are precluded from moving away from each other due to the engagement of the first and second ends 586 and 588 with the thick and thin tissue 518 and 520, as shown in FIGS. 5F and 5G. As discussed herein with respect to FIGS. 2F-2I, in various embodiments, the fastening member 572 can include structures that can engage and pierce the thick and thin tissue of the passage. For example, in various embodiments, the base portion 590 can include a barbed structure 543 designed to engage and pierce tissue of the passage once the first end 572 has engaged thin tissue 520 and the thin tissue 520 has been pulled into contact with the thick tissue 518. The barbed structure 543 can help to maintain contact between the thick and thin tissue 518 and 520 while the second end 588 assumes its expanded state upon being released from the piercing member 570. Once the operator is satisfied with the positioning of the fastening member, the catheter and the positioning device can be extracted from the patient leaving the fastening member 572 behind to effectively occlude the patent foramen ovale 516, as shown in FIG. 5G.

In the embodiments illustrated in FIGS. 6A-6C, a piercing member 645 is illustrated. The piercing member 645 illustrated in FIGS. 6A-6C can function to pierce the tissue of the passage, bring the tissue together, and fastens the tissue to effectively seal a PFO. Thus, in the embodiments illustrated in FIGS. 6A-6C, a fastening member, such as fastening member 272 illustrated in FIGS. 2F-2I is not needed in these embodiments.

FIG. 6A illustrates a first end 647 of the piercing member 645. FIG. 6B illustrates a second end 651 of the piercing member 645. FIG. 6C illustrates the piercing member 645 having the first end 647 and the second end 651 coupled together. In addition, FIG. 6C also illustrates the third deployment shaft 607 coupled to the second end 651 of the piercing member 645.

The piercing member 645 includes an elongate body 647 having the first end 649 and the second end 651. The first end 649 includes a piercing structure 653. As shown in FIGS. 6B and 6C, the piercing structure 653 includes a pointed tip that allows the piercing member 645 to pierce the tissue of passage. In addition, the piercing structure 653 includes a first surface 655. The first surface 655 extends away from the elongate body 647 of the piercing member 645. As shown in FIGS. 6B and 6C, the first surface 655 extends away perpendicularly relative to the elongate body 647. In various embodiments, the first surface 655 provides for a surface in which tissue of the passage can engage (i.e., first surface abuts thin tissue of the passage of a PFO) after the piercing structure 653 has pierced the tissue. The first end 649 also includes an inner surface that defines female threads 657. In various embodiments, these female threads can be designed to be self locking when mated with male threads, as will be discussed herein.

The second end 651 includes a cap 659. The cap 659 includes a second surface 661 that also extends away from the elongate body 647. As shown in FIGS. 6A and 6C, the second surface 661 extends away perpendicularly relative to the elongate body 647. Similar to the first surface 655, the second surface 661 provides for a surface in which tissue of the passage can also engage (i.e., second surface abuts thick tissue of the passage of a PFO), as described herein. The second end 651 also includes an outer surface that defines male threads 663 along a portion of the outer surface. In addition, the second end 651 includes an inner surface that defines female threads 657. In various embodiments, the female threads 657 on the second end are not designed to be self locking when mated with male threads, as will be discussed herein.

In one embodiment, occluding the passage can be accomplished by fastening the thick and thin tissue so as to preclude substances such as blood, blood clots, and the like, from moving through the passage. To do this, the length of the elongate body 647 can be effectively adjusted. Adjusting the length of the elongate body 647 of the piercing device once it has pierced the thick and thin tissue can help to maintain the occlusion of the passage.

In various embodiments, a deployment shaft 665 can be used to adjust the length of the elongate body 647 of the piercing member. In such an embodiment, the deployment shaft 665 can be used to screw the second end 651 into the first end 649 a desired distance so as to adjust the length of the elongate body 647 of the piercing member 645. For example, in one embodiment, female threads 627 on the second end 651 of the elongate body 647 can be designed to accommodate a clockwise and a counterclockwise motion of the third deployment shaft 665. In addition, the female threads 657 can terminate at a predetermined point along the inner surface of the second end 651. The predetermined point can be designed to prevent the deployment shaft 665 from screwing further into the second end 651 such that any rotation by the deployment shaft 665 at the predetermined point is transferred to the second end 651. That is, if the deployment shaft 665 continues to rotate once it reaches the predetermined point within the second end 651, a rotational torque is imparted to the second end 651 of the piercing member 645. This rotational torque causes the second end 651 to rotate such that the male threads 663 on the second end 651 begin to mate with the female 657 threads on the first end 649. As the second end 651 is threaded into the first end 649, the length of the elongate body 647 begins to decrease.

In one embodiment, the male threads 663 on the second end 651 and the female threads 657 on the first end 649 are designed to preclude an unthreading of the first and second ends 649 and 651. Such a design can include, but is not limited to, male threads that deform as they mate with the female threads, or female threads that deform as they mate with the male thread. In such an embodiment, the piercing member 645 can be adjusted to the desired length and locked to that length. The adjustable and self-locking nature of the elongate body 647 seals the passage maintains the occlusion of the passage.

As the reader will appreciate, the piercing member can include a number of designs and configurations, and thus, the piercing member illustrated in FIGS. 6A-6C is not intended to limit the present disclosure to the embodiment illustrated. For example, in some embodiments, the piercing member can include a ball and socket approach in which the first end includes a socket and the second end includes a ball.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:
a positioning device having an elongate body with a proximal end and a distal end, the elongate body includes a wall that extends from the distal end toward the proximal end to a surface that extends away from the wall, the wall defines a wall opening, the elongate body includes a first lumen, a second lumen, a third lumen, and a channel, where the first lumen extends toward the surface, the second lumen extends toward the distal end of the elongate body, the third lumen extends from the wall opening and completely through the distal end of the elongate body to a transverse opening to define the third lumen, and the channel is defined by a surface of the elongate body;
an elongate structure having two pivots coupled to an outer surface of the elongate structure, where the elongate structure is releasably positioned within the second lumen toward the distal end of the positioning device, the second lumen, the channel, and the third lumen form a contiguous conduit for the elongate structure, and the two pivots rotate the elongate structure from the channel to the third lumen;
an extension member slidably positioned within the first lumen; and
a fastening member releasably positioned within a lumen of the elongate structure.

2. The apparatus of claim 1, where the extension member includes an arm that extends away from the surface that extends away from the wall when moved through the ledge opening.

3. The apparatus of claim 2, where the arm extends away from the surface that extends away from the wall within a single plane.

4. The apparatus of claim 2, where the arm extends away from the surface that extends away from the wall in a number of different planes.

5. The apparatus of claim 1, where the extension member includes at least two arms that extend away from the surface in opposite directions.

6. The apparatus of claim 1, where the extension member includes at least two arms that extend away from the surface in different directions and in different planes.

7. The apparatus of claim 1, where the channel extends longitudinally between the second lumen and the third lumen.

8. The apparatus of claim 1, where the elongate structure includes a flexible portion along which the elongate structure bends under a compression force to push the elongate structure away from the channel of the elongate body.

9. The apparatus of claim 8, where the two pivots rotate the elongate structure from the channel to the third lumen under a compression force from a first position to a second position.

10. The apparatus of claim 9, where the two pivots are coupled to the distal end of the elongate structure.

11. The apparatus of claim 1, where the fastening member is releasably positioned within a lumen of a piercing member, the piercing member slidably positioned within the lumen of the elongate structure.

12. The apparatus of claim 11, where a first end and a second end of the fastening member radially extend relative to a base portion of the fastening member when released from the lumen of the piercing member.

13. A system, comprising:
a positioning device including:
an elongate body with a proximal end and a distal end, the elongate body includes a wall that extends from the distal end toward the proximal end to a surface that extends away from the wall, the wall defines a wall opening, the elongate body includes a first lumen, a second lumen, a third lumen, and a channel, where the first lumen extends toward the surface, the second lumen extends toward the distal end of the elongate body, the third lumen extends from the wall opening and completely through the distal end of the elongate body to a transverse opening to define the third lumen, and the channel is defined by a surface of the elongate body;
an elongate structure having two pivots coupled to an outer surface of the elongate structure, where the elongate structure is releasably positioned within the second lumen toward the distal end of the positioning device, the second lumen, the channel, and the third lumen form a contiguous conduit for the elongate structure, and the two pivots rotate the elongate structure from the channel to the third lumen;
a fastening member releasably positioned within a lumen of the elongate structure;
an extension member slidably positioned within the first lumen; and
a catheter including a proximal end and a distal end, the positioning device located between the proximal end and the distal end of the catheter.

14. The system of claim 13, where the positioning device is slidably positioned within a lumen of the catheter toward the distal end of the catheter to deploy the positioning device from the distal end of the catheter.

15. The system of claim 13, where the first lumen of the elongate body includes a first deployment shaft therein and adjacent the proximal end of the extension member, the first deployment shaft moves within the first lumen of the elongate body to push the extension member from the first lumen of the elongate body.

16. The system of claim 13, where the second lumen of the elongate body includes a second deployment shaft therein and adjacent the proximal end of the elongate structure, the second deployment shaft moves within the second lumen of the elongate body to extend the elongate structure away from the elongate body.

17. The system of claim 13, including a third deployment shaft positioned within a lumen of the elongate structure and adjacent a slidably positioned piercing member, the third deployment shaft moves within the lumen of the elongate structure to move a portion of the piercing member through the third lumen of the elongate body and away from the wall.

18. The system of claim 13, including a fourth deployment shaft positioned within the lumen of the elongate structure and adjacent a releasably positioned fastening member, the fourth deployment shaft moves within the lumen of the elongate structure and a lumen of the piercing member to release the fastening member from the lumen of the piercing member.

19. The system of claim 13, where the extension member includes at least one arm that extends away from the surface when extended from the first lumen.

20. The system of claim 13, including a sheath having a proximal end and a distal end, the positioning device coupled to the sheath at the distal end of the sheath, the sheath slidably positioned within a lumen of the catheter to deploy the positioning device from the distal end of the catheter.

21. The system of claim 20, where the sheath includes a first lumen having a first deployment shaft therein and adjacent the proximal end of the extension member, the first deployment shaft moves within the first lumen of the sheath and the first lumen of the elongate body to extend the extension member from the first lumen of the elongate body.

22. The system of claim 20, where the sheath includes a second lumen having a second deployment shaft positioned therein and adjacent the proximal end of the elongate structure, where the second deployment shaft moves within the second lumen of the sheath and the second lumen of the elongate body to extend the elongate structure away from the channel of the elongate body via the channel.

23. The system of claim 20, where the sheath includes a third lumen having a third deployment shaft positioned therein and adjacent the slidably positioned piercing member, the third deployment shaft moves within the third lumen of the sheath and the lumen of the elongate structure to move a portion of the piercing member through the third lumen of the elongate body and away from the wall.

24. The system of claim 20, where the sheath includes a fourth lumen having a fourth deployment shaft positioned therein and adjacent a releasably positioned fastening member, the fourth deployment shaft moves within the fourth lumen of the sheath and the lumen of the elongate structure and a lumen of the piercing member to release the fastening member from the lumen of the piercing member.

25. A method, comprising:
forming a positioning device that includes:
an elongate body with a proximal end and a distal end, the elongate body includes a wall that extends from the distal end toward the proximal end to a surface that extends away from the wall, the wall defines a wall opening, the elongate body includes a first lumen, a second lumen, a third lumen, and a channel, where the first lumen extends toward the surface, the second lumen extends toward the distal end of the elongate body, the third lumen extends from the wall opening and completely through the distal end of the elongate body to a transverse opening to define the third lumen, and the channel is defined by a surface of the elongate body;
an elongate structure having two pivots coupled to an outer surface of the elongate structure, where the elongate structure is extendably positioned within the second lumen toward the distal end of the positioning device, the second lumen, the channel, and the third lumen form a contiguous conduit for the elongate structure, and the two pivots rotate the elongate structure from the channel to the third lumen;
an extension member extendably positioned within the first lumen;
a fastening member releasably positioned within a lumen of the elongate structure; and
slidably coupling the positioning device within a lumen of a catheter between a proximal and a distal end of the catheter.

26. The method of claim 25, where forming the positioning device includes forming a piercing member releasably positioned within the lumen of the elongate structure and releasably positioning the fastening member within a lumen of the piercing member.

* * * * *